United States Patent
Tarby

(10) Patent No.: US 6,844,340 B2
(45) Date of Patent: Jan. 18, 2005

(54) TRICYCLIC 2-PYRIMIDONE COMPOUNDS USEFUL AS HIV REVERSE TRANSCRIPTASE INHIBITORS

(75) Inventor: Christine M. Tarby, Hockessin, DE (US)

(73) Assignee: Bristol-Myers Squibb Company, Princeton, NJ (US)

( * ) Notice: Subject to any disclaimer, the term of this patent is extended or adjusted under 35 U.S.C. 154(b) by 70 days.

(21) Appl. No.: 10/346,613

(22) Filed: Jan. 17, 2003

(65) Prior Publication Data

US 2003/0162800 A1 Aug. 28, 2003

Related U.S. Application Data

(60) Provisional application No. 60/349,641, filed on Jan. 18, 2002.

(51) Int. Cl.[7] .................. C07D 471/04; C07D 471/14; C07D 487/04; A61K 31/53; A61P 31/18
(52) U.S. Cl. ................... 514/248; 514/267; 544/234; 544/249; 544/250; 544/251
(58) Field of Search ................. 514/248, 250, 514/267; 544/234, 249, 250, 251

(56) References Cited

FOREIGN PATENT DOCUMENTS

| WO | WO 01/29037 | 4/2001 |
|---|---|---|
| WO | WO 02/08226 | 1/2002 |

OTHER PUBLICATIONS

Britikova, N.E. et al., "Some Derivatives of pyrimido[5,4-b]quinoline", Khim. Geterotsikl. Soedin., pp. 117–119 (1974) (English translation of Khim. Geterotsikl. Soedin., No. 1, pp. 131–133 (1974)).

Britikova, N.E. et al., "Study of Nucleophilic Substitution Reactions of 2,4,10–trichloropyrimido[5,4-b]quinoline", Khim. Geterotsikl. Soedin., pp. 482–484 (1974) (English translation of Khim. Geterotsikl. Soedin., No. 4, pp. 554–557 (1974)).

Ueda, et al., "Transformation of Pyrazolo[3,4–c][1,5]benzothiazepines into Quinolines", Chem. Pharm. Bull., pp. 1604–1607, (1984), (32)4.

Besly, et al., J. Chem. Soc., "Potential Antimalarial Derivatives of Triaza–anthracene", pp. 4997–5501 (1957).

Levine, et al., J. Heterocyclic Chem., "Pyrimido[5,4–b]quinolines, II. Reactions at the Heterocyclic Ring–Carbon and Nitrogen Atoms (1)", pp. 611–614 (1974), (14).

Levine, et al., J. Heterocyclic Chem., "Pyrimido[5,4–b]quinolines. I. Synthesis of Substituted Tricyclic Systems Related to Riboflavin (1a).", pp. 91–97 (1972), (9)1.

O'brien, et al., J. Heterocyclic Chem., "Synthesis of 10–Deazariboflavin and Related 2,4–Dioxopyrimido[4,5–b]quinolines (1a)", pp. 99–102 (1970) (7).

Chu, et al., J. Heterocyclic Chem., "Pyrimido[5,4–b] quinolines. III. Synthesis of a 10–Alkyl–Substitued 10–Deazaalloxazines (1a)", pp. 1053–1057 (1977).

Fenner, et al., Arch. Pharm., "Pyrimido[5,4–b]chinoline–10–Deaza–alloxazine", pp. 115–125, (1978).

Fenner, et al., "Pyrimido[4,5–c] quinolines from 10–Cyanopyrimido[5,4–b]quinolines", Arch. Pharm., pp. 382–384 (1986), (319)4.

Fenner, et al., "Pyrimido[5,4–b]quinolines by Trialkylphosphite–Cyclisation of 2–Nitro–6'–benzylpyrimidindiones", Arch.Pharm., pp. 379–381 (1986), (319)4.

Primary Examiner—Mukund J. Shah
Assistant Examiner—Thomas McKenzie
(74) Attorney, Agent, or Firm—Mary VanAtten

(57) ABSTRACT

The present invention relates to tricyclic 2-pyrimidone compounds of formula (I):

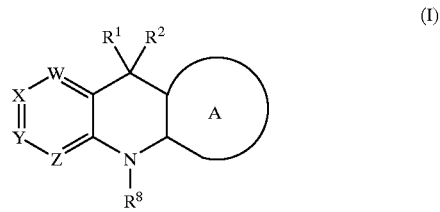

or stereoisomeric forms, stereoisomeric mixtures, or pharmaceutically acceptable salt forms thereof, which are useful as inhibitors of HIV reverse transcriptase, and to pharmaceutical compositions and diagnostic kits comprising the same, and methods of using the same for treating viral infection or as an assay standard or reagent.

32 Claims, No Drawings

TRICYCLIC 2-PYRIMIDONE COMPOUNDS USEFUL AS HIV REVERSE TRANSCRIPTASE INHIBITORS

This application claims benefit to provisional application U.S. Ser. No. 60/349,641 filed Jan. 18, 2002. The entire teachings of the referenced application are incorporated herein by reference.

FIELD OF THE INVENTION

This invention relates generally to tricyclic pyrimidone compounds which are useful as inhibitors of HIV reverse transcriptase, pharmaceutical compositions and diagnostic kits comprising the same, methods of using the same for treating viral infection or as assay standards or reagents, and intermediates and processes for making such tricyclic compounds.

BACKGROUND OF THE INVENTION

Two distinct retroviruses, human immunodeficiency virus (HIV) type-1 (HIV-1) or type-2 (HIV-2), have been etiologically linked to the immunosuppressive disease, acquired immunodeficiency syndrome (AIDS). HIV seropositive individuals are initially asymptomatic but typically develop AIDS related complex (ARC) followed by AIDS. Affected individuals exhibit severe immunosuppression which predisposes them to debilitating and ultimately fatal opportunistic infections.

The disease AIDS is the consequence of HIV-1 or HIV-2 virus following its complex viral life cycle. The virion life cycle involves the virion attaching itself to the host human T-4 lymphocyte immune cell through the binding of a glycoprotein on the surface of the virion's protective coat with the CD4 glycoprotein on the lymphocyte cell. Once attached, the virion sheds its glycoprotein coat, penetrates into the membrane of the host cell, and uncoats its RNA. The virion enzyme, reverse transcriptase, directs the process of transcribing the RNA into single-stranded DNA. The viral RNA is degraded and a second DNA strand is created. The now double-stranded DNA is integrated into the human cell's genes and those genes are used for virus reproduction.

RNA polymerase transcribes the integrated viral DNA into viral mRNA. The viral RNA is translated into the precursor gag-pol fusion polyprotein. The polyprotein is then cleaved by the HIV protease enzyme to yield the mature viral proteins. Thus, HIV protease is responsible for regulating a cascade of cleavage events that lead to the virus particle's maturing into a virus that is capable of full infectivity.

The typical human immune system response, killing the invading virion, is taxed because the virus infects and kills the immune system's T cells. In addition, viral reverse transcriptase, the enzyme used in making a new virion particle, is not very specific, and causes transcription mistakes that result in continually changed glycoproteins on the surface of the viral protective coat. This lack of specificity decreases the immune system's effectiveness because antibodies specifically produced against one glycoprotein may be useless against another, hence reducing the number of antibodies available to fight the virus. The virus continues to reproduce while the immune response system continues to weaken. In most cases, without therapeutic intervention, HIV causes the host's immune system to be debilitated, allowing opportunistic infections to set in. Without the administration of antiviral agents, immunomodulators, or both, death may result.

There are at least three critical points in the HIV life cycle which have been identified as possible targets for antiviral drugs: (1) the initial attachment of the virion to the T-4 lymphocyte or macrophage site, (2) the transcription of viral RNA to viral DNA (reverse transcriptase, RT), and (3) the processing of gag-pol protein by HIV protease.

Inhibition of the virus at the second critical point, the viral RNA to viral DNA transcription process, has provided a number of the current therapies used in treating AIDS. This transcription must occur for the virion to reproduce because the virion's genes are encoded in RNA and the host cell transcribes only DNA. By introducing drugs that block the reverse transcriptase from completing the formation of viral DNA, HIV-1 replication can be stopped.

A number of compounds that interfere with viral replication have been developed to treat AIDS. For example, nucleoside analogs, such as 3'-azido-3'-deoxythymidine (AZT), 2',3'-dideoxycytidine (ddC), 2',3'-dideoxythymidinene (d4T), 2',3'-dideoxyinosine (ddI), and 2',3'-dideoxy-3'-thia-cytidine (3TC) have been shown to be relatively effective in certain cases in halting HIV replication at the reverse transcriptase (RT) stage.

An active area of research is in the discovery of non-nucleoside HIV reverse transcriptase inhibitors (NNRTIs). As an example, it has been found that certain benzoxazinones and quinazolinones are active in the inhibition of HIV reverse transcriptase, the prevention or treatment of infection by HIV and the treatment of AIDS.

U.S. Pat. No. 5,874,430 describes benzoxazinone non-nucleoside reverse transcriptase inhibitors for the treatment of HIV. U.S. Pat. No. 5,519,021 describe non-nucleoside reverse transcriptase inhibitors which are benzoxazinones of the formula:

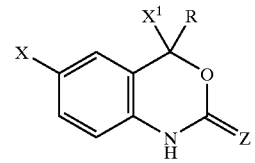

wherein X is a halogen, Z may be O.

EP 0,530,994 and WO 93/04047 describe HIV reverse transcriptase inhibitors which are quinazolinones of the formula (A):

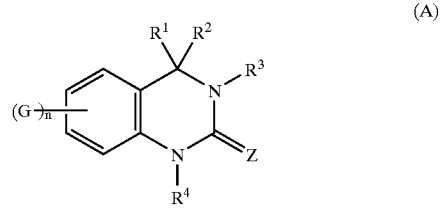

(A)

wherein G is a variety of groups, $R^3$ and $R^4$ may be H, Z may be O, $R^2$ may be unsubstituted alkyl, unsubstituted alkenyl, unsubstituted alkynyl, unsubstituted cycloalkyl, unsubstituted heterocycle, and optionally substituted aryl, and $R^1$ may be a variety of groups including substituted alkyl.

WO 95/12583 also describes HIV reverse transcriptase inhibitors of formula A. In this publication, G is a variety of groups, $R^3$ and $R^4$ may be H, Z may be O, $R^2$ is substituted alkenyl or substituted alkynyl, and $R^1$ is cycloalkyl, alkynyl, alkenyl, or cyano. WO 95/13273 illustrates the asymmetric synthesis of one of the compounds of WO 95/12583, (S)-

(−)-6-chloro-4-cyclopropyl-3,4-dihydro-4((2-pyridy)ethynyl)-2(1H)-quinazolinone.

Synthetic procedures for making quinazolinones like those described above are detailed in the following references: Houpis et al., *Tetr. Lett.* 1994, 35(37), 6811–6814; Tucker et al., *J. Med. Chem.* 1994, 37, 2437–2444; and, Huffman et al., *J. Org. Chem.* 1995, 60, 1590–1594.

DE 4,320,347 illustrates quinazolinones of the formula:

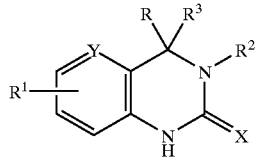

wherein R is a phenyl, carbocyclic ring, or a heterocyclic ring. Compounds of this sort are not considered to be part of the present invention.

WO 01/29037 describes HIV reverse transcriptase inhibitors of the formula

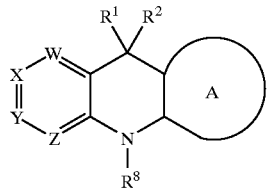

wherein the A ring is a heteroaryl ring containing one or two nitrogen atoms.

Even with the current success of reverse transcriptase inhibitors, it has been found that HIV patients can become resistant to a given inhibitor. Thus, there is an important need to develop additional inhibitors to further combat HIV infection.

SUMMARY OF THE INVENTION

Accordingly, the present invention provides novel reverse transcriptase inhibitors.

The present invention provides a novel method for treating HIV infection which comprises administering to a host in need of such treatment a therapeutically effective amount of at least one of the compounds of the present invention, including a pharmaceutically acceptable salt form thereof.

The present invention provides a novel method for treating HIV infection which comprises administering to a host in need thereof a therapeutically effective combination of (a) one of the compounds of the present invention and (b) one or more compounds selected from the group consisting of HIV reverse transcriptase inhibitors and HIV protease inhibitors.

The present invention provides pharmaceutical compositions with reverse transcriptase inhibiting activity comprising a pharmaceutically acceptable carrier and a therapeutically effective amount of at least one of the compounds of the present invention or a pharmaceutically acceptable salt form thereof.

The present invention provides novel tricyclic pyrimidone compounds for use in therapy.

The present invention provides the use of novel tricyclic pyrimidone compounds for the manufacture of a medicament for the treatment of HIV infection.

These and other aspects of the invention, which will become apparent during the following detailed description, have been achieved by the inventors' discovery that compounds of formula (I):

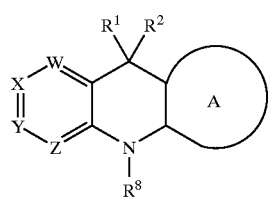

wherein ring A, $R^1$, $R^2$, $R^8$, A, W, X, Y, and Z are defined below, including any stereoisomeric form, mixtures of stereoisomeric forms, complexes, prodrug forms or pharmaceutically acceptable salt forms thereof, are effective reverse transcriptase inhibitors.

DETAILED DESCRIPTION OF EMBODIMENTS

[1] Thus, in an embodiment, the present invention provides a novel compound of formula (I):

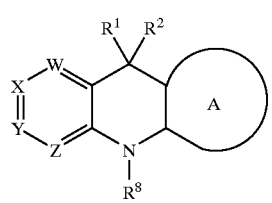

or a stereoisomeric form or mixture of stereoisomeric forms or a pharmaceutically acceptable salt form thereof, wherein:

A is a ring selected from:

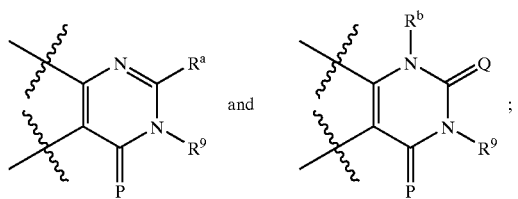

P is O or S;

Q is O or NH;

$R^a$ is selected from H, CN, $C_{1-4}$ alkyl, $C_{1-4}$ alkenyl, $C_{1-4}$ alkynyl, OH, $C_{1-4}$ alkyl-O—, $C_{1-4}$ alkyl-NH—, and $NH_2$;

$R^b$ is selected from H, $C_{1-4}$ alkyl, $C_{1-4}$ alkenyl, and $C_{1-4}$ alkynyl;

W is N or $CR^3$;

X is N or $CR^{3a}$;

Y is N or $CR^{3b}$;

Z is N or $CR^{3c}$;

provided that if two of W, X, Y, and Z are N, then the remaining are other than N;

$R^1$ is selected from the group cyclopropyl, hydroxymethyl, CN, and $C_{1-4}$ alkyl substituted with 0–9 halogen;

$R^2$ is selected from the group methyl substituted with 0–3 $R^{3f}$, $C_{1-6}$ alkyl substituted with 0–2 $R^4$, $C_{2-6}$ haloalkyl, $C_{2-5}$ alkenyl substituted with 0–2 $R^4$, $C_{2-5}$ alkynyl substituted with 0–1 $R^4$, $C_{3-6}$ cycloalkyl substituted with 0–2 $R^{3d}$, phenyl substituted with 0–2 $R^{3d}$, and 3–6 membered heterocyclic system containing 1–3 heteroatoms selected from the group O, N, and S, substituted with 0–2 $R^{3d}$;

$R^3$ is selected from the group H, $C_{1-4}$ alkyl, —OH, $C_{1-4}$ alkoxy, $OCF_3$, $CF_3$, F, Cl, Br, I, —$(CH_2)_r NR^5R^{5a}$, —$NO_2$, —CN, —$C(O)R^6$, —$(CH_2)_r NHC(O)R^7$, —$(CH_2)_r NHC(O)NR^5R^{5a}$, —$NHSO_2R^{10}$, —S—$C_{1-4}$ alkyl, —$S(O)C_{1-4}$alkyl, —$S(O)_2C_{1-4}$alkyl, —$SO_2NR^5R^{5a}$, and a 5–6 membered heteroaromatic ring containing 1–4 heteroatoms selected from the group O, N, and S;

$R^{3a}$ is selected from the group H, $C_{1-4}$ alkyl, —OH, $C_{1-4}$ alkoxy, $OCF_3$, $CF_3$, F, Cl, Br, I, —$(CH_2)_r NR^5R^{5a}$, —$NO_2$, —CN, —$C(O)R^6$, —$(CH_2)_r NHC(O)R^7$, —$(CH_2)_r NHC(O)NR^5R^{5a}$, —$NHSO_2R^{10}$, —S—$C_{1-4}$ alkyl, —$S(O)C_{1-4}$alkyl, —$S(O)_2C_{1-4}$alkyl, —$SO_2NR^5R^{5a}$, and a 5–6 membered heteroaromatic ring containing 1–4 heteroatoms selected from the group O, N, and S;

alternatively, $R^3$ and $R^{3a}$ together form —$OCH_2O$—;

$R^{3b}$ is selected from the group H, $C_{1-4}$ alkyl, —OH, $C_{1-4}$ alkoxy, $OCF_3$, F, Cl, Br, I, —$NR^5R^{5a}$, —$NO_2$, —CN, —$C(O)R^6$, —$NHC(O)R^7$, —$NHC(O)NR^5R^{5a}$, —$NHSO_2R^{10}$, and —$SO_2NR^5R^{5a}$;

alternatively, $R^{3a}$ and $R^{3b}$ together form —$OCH_2O$—;

$R^{3c}$ is selected from the group H, $C_{1-4}$ alkyl, —OH, $C_{1-4}$ alkoxy, $OCF_3$, F, Cl, Br, I, —$NR^5R^{5a}$, —$NO_2$, —CN, —$C(O)R^6$, —$NHC(O)R^7$, —$NHC(O)NR^5R^{5a}$, —$NHSO_2R^{10}$, and —$SO_2NR^5R^{5a}$;

alternatively, $R^{3b}$ and $R^{3c}$ together form —$OCH_2O$—;

$R^{3d}$, at each occurrence, is independently selected from the group H, $C_{1-4}$ alkyl, —OH, $C_{1-4}$ alkoxy, $OCF_3$, F, Cl, Br, I, —$NR^5R^{5a}$, —$NO_2$, —CN, —$C(O)R^6$, —$NHC(O)R^7$, —$NHC(O)NR^5R^{5a}$, —$NHSO_2R^{10}$, and —$SO_2NR^5R^{5a}$;

$R^{3e}$, at each occurrence, is independently selected from the group H, $C_{1-4}$ alkyl, —OH, $C_{1-4}$ alkoxy, $OCF_3$, F, Cl, Br, I, —$NR^5R^{5a}$, —$NO_2$, —CN, —$C(O)R^6$, —$NHC(O)R^7$, —$NHC(O)NR^5R^{5a}$, —$NHSO_2R^{10}$, and —$SO_2NR^5R^{5a}$;

$R^{3f}$, at each occurrence, is independently selected from the group H, F, Cl, Br, I, $C_{1-4}$ alkyl, CN, —OH, —O—$R^{11}$, $OCF_3$, —$O(CO)$—$R^{13}$, —OS $(O)_2C_{1-4}$ alkyl, —$NR^{12}R^{12a}$, —$C(O)R^{13}$, —$NHC(O)R^{13}$, —$SR^{11}$, —$S(O)R^{11}$, —$S(O)_2R^{11}$, —$NHSO_2R^{10}$, and —$SO_2NR^{12}R^{12a}$;

$R^4$ is selected from the group H, F, Cl, Br, I, $C_{1-6}$ alkyl substituted with 0–2 $R^{3e}$, $C_{3-10}$ carbocycle substituted with 0–2 $R^{3e}$, phenyl substituted with 0–5 $R^{3e}$, and a 5–10 membered heterocyclic system containing 1–3 heteroatoms selected from the group O, N, and S, substituted with 0–2 $R^{3e}$;

$R^5$ and $R^{5a}$ are independently selected from the group H and $C_{1-4}$ alkyl;

alternatively, $R^5$ and $R^{5a}$, together with the nitrogen to which they are attached, combine to form a 5–6 membered ring containing 0–1 O or N atoms;

$R^6$ is selected from the group H, OH, $C_{1-4}$ alkyl, $C_{1-4}$ alkoxy, and $NR^5R^{5a}$;

$R^7$ is selected from the group H, $C_{1-3}$ alkyl and $C_{1-3}$ alkoxy;

$R^8$ is selected from the group H, $(C_{1-6}$ alkyl)carbonyl, $C_{1-6}$ alkoxy, $(C_{1-4}$ alkoxy)carbonyl, $C_{6-10}$ aryloxy, $(C_{6-10}$ aryl)oxycarbonyl, $(C_{6-10}$ aryl)methylcarbonyl, $(C_{1-4}$ alkyl)carbonyloxy($C_{1-4}$ alkoxy)carbonyl, $C_{6-10}$ arylcarbonyloxy($C_{1-4}$ alkoxy)carbonyl, $C_{1-6}$ alkylaminocarbonyl, phenylaminocarbonyl, phenyl ($C_{1-4}$ alkoxy)carbonyl, and $NR^5R^{5a}(C_{1-6}$ alkyl)carbonyl;

$R^9$ is selected from H, $C_{1-4}$ alkyl, $C_{1-4}$ alkenyl, $C_{1-4}$ alkynyl, $(C_{1-6}$ alkyl)carbonyl, $C_{1-6}$ alkoxy, $(C_{1-4}$ alkoxy)carbonyl, $C_{6-10}$ aryloxy, $(C_{6-10}$ aryl) oxycarbonyl, $(C_{6-10}$ aryl)methylcarbonyl, $(C_{1-4}$ alkyl) carbonyloxy($C_{1-4}$ alkoxy)carbonyl, $C_{6-10}$ arylcarbonyloxy($C_{1-4}$ alkoxy)carbonyl, $C_{1-6}$ alkylaminocarbonyl, phenylaminocarbonyl, phenyl ($C_{1-4}$ alkoxy)carbonyl, and $NR^5R^{5a}(C_{1-6}$ alkyl) carbonyl;

$R^{10}$ is selected from the group $C_{1-4}$ alkyl and phenyl;

$R^{11}$ is selected from $C_{1-6}$ alkyl, $C_{1-6}$ haloalkyl, $C_{1-6}$ alkyl substituted with $C_{3-6}$cycloalkyl substituted with 0–2 $R^{3e}$, $C_{2-6}$ alkenyl, $C_{2-6}$ alkynyl, $C_{3-6}$ carbocycle substituted with 0–2 $R^{3e}$;

$R^{12}$ and $R^{12a}$ are independently selected from H, $C_{1-6}$ alkyl, $C_{1-6}$ alkyl substituted with $C_{3-6}$cycloalkyl substituted with 0–2 $R^{3e}$, and $C_{3-6}$ carbocycle substituted with 0–2 $R^{3e}$;

alternatively, $R^{12}$ and $R^{12a}$ can join to form 4–7 membered heterocyclic ring;

$R^{13}$ is selected from the group H, $C_{1-6}$ alkyl, $C_{1-6}$ haloalkyl, $C_{1-6}$ alkoxy, $C_{2-6}$ alkenyl, $C_{2-6}$ alkynyl, —O—$C_{2-6}$ alkenyl, —O—$C_{2-6}$ alkynyl, $NR^{12}R^{12a}$, $C_{3-6}$carbocycle, and —O—$C_{3-6}$carbocycle; and t is selected from 0 and 1.

[2] In another embodiment, the present invention provides compounds of formula (I), wherein:

$R^2$ is selected from the group methyl substituted with 0–3 $R^{3f}$, $C_{1-5}$ alkyl substituted with 0–2 $R^4$, $C_{2-5}$ alkenyl substituted with 0–2 $R^4$, $C_{2-5}$ alkynyl substituted with 0–1 $R^4$, $C_{3-6}$ cycloalkyl substituted with 0–2 $R^{3d}$, and phenyl substituted with 0–2 $R^{3d}$, and 3–6 membered heterocyclic system containing 1–3 heteroatoms selected from the group O, N, and S, substituted with 0–2 $R^{3d}$, wherein the heterocyclic system is selected from 2-pyridyl, 3-pyridyl, 4-pyridyl, 2-furanyl, 3-furanyl, 2-thienyl, 3-thienyl, 2-oxazolyl, 2-thiazolyl, 4-isoxazolyl, 2-imidazolyl, pyrazolyl, triazolyl, 1,3-dioxolanyl, and 1,3-dioxanyl;

$R^3$ and $R^{3a}$, at each occurrence, are independently selected from the group H, $C_{1-4}$ alkyl, OH, $C_{1-4}$ alkoxy, F, Cl, Br, I, $NR^5R^{5a}$, $NO_2$, —CN, $C(O)R^6$, $NHC(O)R^7$, $NHC(O)NR^5R^{5a}$, and a 5–6 membered heteroaromatic ring containing 1–4 heteroatoms selected from the group O, N, and S;

alternatively, $R^3$ and $R^{3a}$ together form —$OCH_2O$—;

$R^{3b}$ and $R^{3c}$, at each occurrence, are independently selected from the group H, $C_{1-4}$ alkyl, OH, $C_{1-4}$ alkoxy, F, Cl, Br, I, $NR^5R^{5a}$, $NO_2$, —CN, $C(O)R^6$, $NHC(O)R^7$, and $NHC(O)NR^5R^{5a}$;

alternatively, $R^{3a}$ and $R^{3b}$ together form —$OCH_2O$—;

$R^4$ is selected from the group H, Cl, F, $C_{1-4}$ alkyl substituted with 0–2 $R^{3e}$, $C_{3-6}$ carbocycle substituted with 0–2 $R^{3e}$, phenyl substituted with 0–5 $R^{3e}$, and a 5–6 membered heterocyclic system containing 1–3 heteroatoms selected from the group O, N, and S, substituted with 0–2 $R^{3e}$;

$R^5$ and $R^{5a}$ are independently selected from the group H, $CH_3$ and $C_2H_5$;

$R^6$ is selected from the group H, OH, $CH_3$, $C_2H_5$, $OCH_3$, $OC_2H_5$, and $NR^5R^{5a}$; and $R^7$ is selected from the group $CH_3$, $C_2H_5$, $CH(CH_3)_2$, $OCH_3$, $OC_2H_5$, and $OCH(CH_3)_2$.

[3] In another embodiment, the present invention provides compounds of formula (I), wherein:

P is O;

Ring A is:

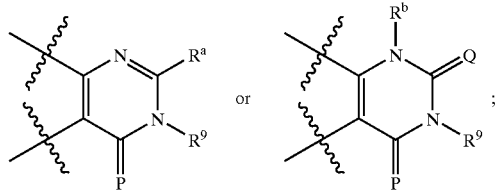

$R^a$, at each occurrence, is selected from H, $C_{1-4}$ alkyl, $C_{1-4}$ alkyl-NH—, $NH_2$;

$R^c$ is selected from H and methyl;

W is $CR^3$;

X is $CR^{3a}$;

Y is $CR^{3b}$;

Z is $CR^{3c}$;

$R^2$ is selected from the group methyl substituted with 0–3 $R^{3f}$, $C_{1-3}$ alkyl substituted with 0–2 $R^4$, $C_{2-3}$ alkenyl substituted with 0–2 $R^4$, $C_{2-3}$ alkynyl substituted with 0–1 $R^4$, and $C_{3-6}$ cycloalkyl substituted with 0–2 $R^{3d}$;

$R^3$, $R^{3a}$, $R^{3b}$, and $R^{3c}$, at each occurrence, are independently selected from the group H, $C_{1-3}$ alkyl, OH, $C_{1-3}$ alkoxy, F, Cl, Br, I, $NR^5R^{5a}$, $NO_2$, —CN, $C(O)R^6$, $NHC(O)R^7$, and $NHC(O)NR^5R^{5a}$;

alternatively, $R^3$ and $R^{3a}$ together form —$OCH_2O$—;

$R^{3e}$, at each occurrence, is independently selected from the group H, $C_{1-4}$ alkyl, —OH, $C_{1-4}$ alkoxy, $OCF_3$, F, Cl, —$NR^5R^{5a}$, —$C(O)R^6$, and —$SO_2NR^5R^{5a}$;

$R^{3f}$, at each occurrence, is independently selected from the group H, F, Cl, Br, I, $C_{1-4}$ alkyl, CN, —OH, —O—$R^{11}$, —O(CO)—$R^{13}$, —$SR^{11}$, —$S(O)R^{11}$, —$S(O)_2R^{11}$, and —$NR^{12}R^{12a}$;

$R^4$ is selected from the group H, Cl, F, $C_{1-4}$ alkyl substituted with 0–1 $R^{3e}$, $C_{3-5}$ carbocycle substituted with 0–2 $R^{3e}$, phenyl substituted with 0–2 $R^{3e}$, and a 5–6 membered heterocyclic system containing 1–3 heteroatoms selected from the group O, N, and S, substituted with 0–1 $R^{3e}$, wherein the heterocyclic system is selected from 2-pyridyl, 3-pyridyl, 4-pyridyl, 2-furanyl, 3-furanyl, 2-thienyl, 3-thienyl, 2-oxazolyl, 2-thiazolyl, 4-isoxazolyl, 2-imidazolyl, pyrazolyl, triazolyl, 1,3-dioxolanyl, and 1,3-dioxanyl;

$R^5$ and $R^{5a}$ are independently selected from the group H, $CH_3$ and $C_2H_5$;

$R^6$ is selected from the group H, OH, $CH_3$, $C_2H_5$, $OCH_3$, $OC_2H_5$, and $NR^5R^{5a}$;

$R^7$ is selected from the group $CH_3$, $C_2H_5$, $OCH_3$, and $OC_2H_5$;

$R^8$ is H;

$R^9$ is H, methyl, ethyl, propyl, and i-propyl;

$R^{11}$ is selected from methyl, ethyl, propyl, i-propyl, butyl, i-butyl, t-butyl, and $C_{3-6}$ carbocycle substituted with 0–2 $R^{3e}$ wherein the $C_{3-6}$ carbocycle is selected from cyclopropyl, cyclobutyl, cyclopentyl, cyclohexyl and phenyl; and $R^{12}$ and $R^{12a}$ are independently selected from H, methyl, ethyl, propyl, i-propyl, butyl, i-butyl, t-butyl, and $C_{3-6}$ carbocycle substituted with 0–2 $R^{3e}$ wherein the $C_{3-6}$ carbocycle is selected from cyclopropyl, cyclobutyl, cyclopentyl, cyclohexyl and phenyl.

[4] In another embodiment, the present invention provides compounds of formula (I), wherein:

$R^2$ is selected from the group methyl substituted with 0–3 $R^{3f}$, $C_{1-3}$ alkyl substituted with 1 $R^4$, $C_{2-3}$ alkenyl substituted with 1 $R^4$, and $C_{2-3}$ alkynyl substituted with 1 $R^4$;

$R^3$, $R^{3a}$, $R^{3b}$, and $R^{3c}$, at each occurrence, are independently selected from the group H, $C_{1-3}$ alkyl, OH, $C_{1-3}$ alkoxy, F, Cl, $NR^5R^{5a}$, $NO_2$, —CN, $C(O)R^6$, $NHC(O)R^7$, and $NHC(O)NR^5R^{5a}$;

alternatively, $R^3$ and $R^{3a}$ together form —$OCH_2O$—;

$R^{3e}$, at each occurrence, is independently selected from the group $CH_3$, —OH, $OCH_3$, $OCF_3$, F, Cl, and —$NR^5R^{5a}$;

$R^{3f}$, at each occurrence, is independently selected from the group H, F, Cl, Br, I, $C_{1-4}$ alkyl, —OH, CN, —O—$R^{11}$, —O(CO)—$R^{13}$, and —$NR^{12}R^{12a}$, —$SR^{11}$, —$S(O)R^{11}$, $S(O)_2R^{11}$, and —$OS(O)_2$methyl;

$R^4$ is selected from the group H, Cl, F, $CH_3$, $CH_2CH_3$, cyclopropyl substituted with 0–1 $R^{3e}$, 1-methylcyclopropyl substituted with 0–1 $R^{3e}$, cyclobutyl substituted with 0–1 $R^{3e}$, phenyl substituted with 0–2 $R^{3e}$, and a 5–6 membered heterocyclic system containing 1–3 heteroatoms selected from the group O, N, and S, substituted with 0–1 $R^{3e}$, wherein the heterocyclic system is selected from the group 2-pyridyl, 3-pyridyl, 4-pyridyl, 2-imidazolyl, pyrazolyl, triazolyl, 1,3-dioxolanyl, and 1,3-dioxanyl;

$R^5$ and $R^{5a}$ are independently selected from the group H, $CH_3$ and $C_2H_5$;

$R^6$ is selected from the group H, OH, $CH_3$, $C_2H_5$, $OCH_3$, $OC_2H_5$, and $NR^5R^{5a}$;

$R^7$ is selected from the group $CH_3$, $C_2H_5$, $OCH_3$, and $OC_2H_5$; and $R^9$ is selected from H and methyl.

[5] In another embodiment, the present invention provides compounds of formula (I), wherein:

$R^2$ is selected from the group methyl substituted with 0–2 $R^{3f}$, methyl substituted with 0–2 $R^4$, ethyl substituted with 0–2 $R^4$, propyl substituted with 0–2 $R^4$, ethenyl substituted with 0–2 $R^4$, 1-propenyl substituted with 0–2 $R^4$, 2-propenyl substituted with 0–2 $R^4$, ethynyl substituted with 0–2 $R^4$, 1-propynyl substituted with 0–2 $R^4$, 2-propynyl substituted with 0–2 $R^4$, and cyclopropyl substituted with 0–1 $R^{3d}$;

$R^{3e}$, at each occurrence, is independently selected from the group $CH_3$, —OH, $OCH_3$, $OCF_3$, F, Cl, and —$NR^5R^{5a}$;

$R^4$ is selected from the group H, Cl, F, $CH_3$, $CH_2CH_3$, cyclopropyl substituted with 0–1 $R^{3e}$, 1-methylcyclopropyl substituted with 0–1 $R^{3e}$, cyclobutyl substituted with 0–1 $R^{3e}$, phenyl substituted with 0–2 $R^{3e}$, and a 5–6 membered heterocyclic system containing 1–3 heteroatoms selected from the group O, N, and S, substituted with 0–1 $R^{3e}$, wherein the heterocyclic system is selected from the group 2-pyridyl, 3-pyridyl, 4-pyridyl, 2-imidazolyl, pyrazolyl, triazolyl, 1,3-dioxolanyl, and 1,3-dioxanyl;

$R^5$ and $R^{5a}$ are independently selected from the group H, $CH_3$ and $C_2H_5$;

$R^6$ is selected from the group H, OH, $CH_3$, $C_2H_5$, $OCH_3$, $OC_2H_5$, and $NR^5R^{5a}$;

$R^7$ is selected from the group $CH_3$, $C_2H_5$, $OCH_3$, and $OC_2H_5$;

$R^8$ is H.

[6] In another embodiment, the present invention provides compounds of formula (I), wherein:

$R^1$ is selected from methyl, ethyl, propyl, i-propyl, butyl, cyclopropyl, $CF_3$, $CF_2CH_3$, CN, and hydroxymethyl;

$R^2$ is selected from the group methyl substituted with 0–2 $R^{3f}$, methyl substituted with 0–2 $R^4$, ethyl substituted with 0–2 $R^4$, propyl substituted with 0–1 $R^4$, ethenyl substituted with 0–2 $R^4$, 1-propenyl substituted with 0–2 $R^4$, 2-propenyl substituted with 0–2 $R^4$, ethynyl substituted with 0–2 $R^4$, 1-propynyl substituted with 0–2 $R^4$;

$R^3$, $R^{3b}$, and $R^{3c}$ are H;

$R^{3e}$ is $CH_3$;

$R^{3f}$, at each occurrence, is independently selected from the group H, F, Cl, Br, I, $C_{1-4}$ alkyl, CN, —OH, —O—$R^{11}$, —$SR^{11}$, —$S(O)R^{11}$, —$S(O)_2R^{11}$, and —$NR^{12}R^{12a}$;

$R^4$ is selected from the group H, cyclopropyl substituted with 0–1 $R^{3e}$, and a 5–6 membered heterocyclic system containing 1–3 heteroatoms selected from the group O, N, and S, substituted with 0–1 $R^{3e}$, wherein the heterocyclic system is selected from the group 2-pyridyl, 3-pyridyl, 4-pyridyl, 2-imidazolyl, pyrazolyl, triazolyl, 1,3-dioxolanyl, and 1,3-dioxanyl;

$R^{12}$ and $R^{12a}$ are independently selected from H, methyl, ethyl, propyl, and i-propyl, and $C_{3-6}$ carbocycle substituted with 0–2 $R^{3e}$ wherein the $C_{3-6}$ carbocycle is selected from cyclopropyl.

[7] In another embodiment, the present invention provides compounds of formula (I), wherein:

ring A is

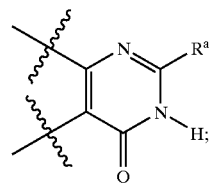

$R^a$ is H, methyl, ethyl, propyl, and i-propyl;

$R^1$ is $CF_3$;

$R^2$ is selected from methyl substituted with 0–1 $R^{3f}$, ethyl, propyl, i-propyl, and butyl;

W is CH;

X is $CR^{3a}$;

Y is CH;

Z is CH;

$R^{3a}$ is selected from H, F, Cl, Br, and CN;

$R^{3f}$ is —O—$R^{11}$;

$R^8$ is H; and $R^{11}$ is selected from methyl, ethyl, propyl, i-propyl, butyl, s-butyl, i-butyl, and t-butyl.

[8] In another embodiment, compounds of the present invention are those compounds wherein the compound is of formula (Ic):

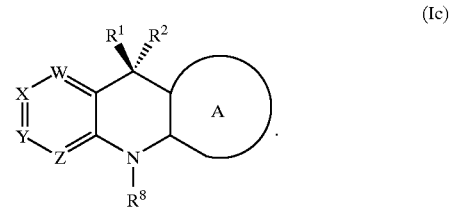

[8] In another embodiment, compounds of the present invention include compounds of formula (I) wherein the compound of formula (I) is selected from is selected from:

10-Butyl-8-chloro-10-(trifluoromethyl)-5,10-dihydropyrimido[5,4-b]quinolin-4(3H)-one;

10-Butyl-8-cyano-10-(trifluoromethyl)-5,10-dihydropyrimido[5,4-b]quinolin-4(3H)-one;

8-Chloro-10-(isopropoxymethyl)-10-(trifluoromethyl)-5,10-dihydropyrimido[5,4-b]quinolin-4(3H)-one;

8-Cyano-10-(isopropoxymethyl)-10-(trifluoromethyl)-5,10-dihydropyrimido[5,4-b]quinolin-4(3H)-one;

10-Butyl-8-chloro-2-methyl-10-(trifluoromethyl)-5,10-dihydropyrimido[5,4-b]quinolin-4(3H)-one;

8-Chloro-10-(isopropoxymethyl)-2-methyl-10-(trifluoromethyl)-5,10-dihydropyrimido[5,4-b]quinolin-4(3H)-one;

8-Cyano-10-(isopropoxymethyl)-2-methyl-10-(trifluoromethyl)-5,10-dihydropyrimido[5,4-b]quinolin-4(3H)-one;

8-Chloro-10-(2-cyclopropylethyl)-10-(trifluoromethyl)-5,10-dihydropyrimido[5,4-b]quinolin-4(3H)-one;

8-Cyano-10-(2-cyclopropylethyl)-10-(trifluoromethyl)-5,10-dihydropyrimido[5,4-b]quinolin-4(3H)-one; and 10-(4-Bromobenzyl)-8-chloro-10-(trifluoromethyl)-5,10-dihydropyrimido [5,4-b] quinolin-4(3H)-one.

The present invention also provides a novel pharmaceutical composition comprising a pharmaceutically acceptable carrier and a therapeutically effective amount of a compound of formula (I) or a pharmaceutically acceptable salt form thereof The compositions and methods of use comprising the compounds of the present invention include compositions and methods of use comprising the compounds of the present invention and stereoisomeric forms thereof, mixtures of stereoisomeric forms thereof, complexes thereof, crystalline forms thereof, prodrug forms thereof and pharmaceutically acceptable salt forms thereof In another embodiment, the present invention provides a novel method for treating HIV infection which comprises administering to a host in need of such treatment a therapeutically effective amount of a compound of formula (I) or a pharmaceutically acceptable salt form thereof In another embodiment, the present invention provides a novel method of treating HIV infection which comprises administering, in combination, to a host in need thereof a therapeutically effective amount of:

(a) a compound of formula (I); and (b) at least one compound selected from the group consisting of HIV reverse transcriptase inhibitors and HIV protease inhibitors.

In another embodiment, the present invention provides a novel method of treating HIV infection which comprises administering, in combination, to a host in need thereof a therapeutically effective amount of:

(a) a compound of formula (I); and (b) at least one compound selected from the group consisting of HIV reverse transcriptase inhibitors, HIV protease inhibitors, CCR-5 inhibitors, and fusion inhibitors.

In another embodiment reverse transcriptase inhibitors useful in the above method of treating HIV infection are selected from the group AZT, ddC, ddI, d4T, 3TC, delavirdine, efavirenz, nevirapine, Ro 18,893, trovirdine, MKC-442, HBY 097, HBY1293, GW867, ACT, UC-781, UC-782, RD4-2025, MEN 10979, AG1549 (S1153), TMC-120, TMC-125, Calanolide A, and PMPA. Protease inhibitors useful in the above method of treating HIV infection are selected from the group saquinavir, ritonavir, indinavir, amprenavir, nelfinavir, palinavir, BMS-232623, GS3333, KNI-413, KNI-272, LG-71350, CGP-61755, PD 173606, PD 177298, PD 178390, PD 178392, U-140690, ABT-378, DMP-450, AG-1776, VX-175, MK-944, and VX-478, the CCR-5 inhibitor is selected from TAK-779 (Takeda), SC-351125 (SCH-C, Schering) and SCH-D (Schering), and the fusion inhibitor is selected from T-20 amd T1249.

In another embodiment, the reverse transcriptase inhibitor is selected from the group AZT, efavirenz, and 3TC and the protease inhibitor is selected from the group saquinavir, ritonavir, nelfinavir, and indinavir.

In another embodiment, the reverse transcriptase inhibitor is AZT.

In another embodiment, the protease inhibitor is indinavir.

In another embodiment, the present invention provides a pharmaceutical kit useful for the treatment of HIV infection, which comprises a therapeutically effective amount of:

(a) a compound of formula (I); and,
(b) at least one compound selected from the group consisting of HIV reverse transcriptase inhibitors and HIV protease inhibitors, in one or more sterile containers.

In another embodiment, the present invention provides novel tricyclic 2-pyrimidone compounds for use in therapy.

In another embodiment, the present invention provides the use of novel tricyclic 2-pyrimidone compounds for the manufacture of a medicament for the treatment of HIV infection.

In another embodiment, the present invention provides that Ring A is

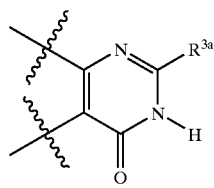

In another embodiment, the present invention provides that Ring A is

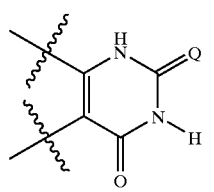

In another embodiment, the present invention provides that $R^1$ is selected from $CF_3$, $CF_2CH_3$, and $CHF_2$.

In another embodiment, the present invention provides that $R^1$ is $CF_3$.

In another embodiment, the present invention provides that $R^1$ is selected from the group $CF_3$, $C_2F_5$, $CF_2CH_3$, $CHF_2$, $CH_2F$ and cyclopropyl.

In another embodiment, the present invention provides that $R^1$ is methyl substituted with 0–3 $R^{3f}$, and $C_{2-5}$ alkyl substituted with 0–2 $R^4$, wherein the $C_{2-5}$ alkyl is selected from ethyl, propyl, i-propyl and butyl.

In another embodiment, the present invention provides that $R^1$ is CN and hydroxymethyl.

In another embodiment, the present invention provides that $R^2$ is selected from the group methyl substituted with 0–3 $R^{3f}$, $C_{1-5}$ alkyl substituted with 0–2 $R^4$, $C_{2-5}$ alkenyl substituted with 0–2 $R^4$, $C_{2-5}$ alkynyl substituted with 0–1 $R^4$, $C_{3-6}$ cycloalkyl substituted with 0–2 $R^{3d}$, and phenyl substituted with 0–2 $R^{3d}$, and 3–6 membered heterocyclic system containing 1–3 heteroatoms selected from the group O, N, and S, substituted with 0–2 $R^{3d}$, wherein the heterocyclic system is selected from 2-pyridyl, 3-pyridyl, 4-pyridyl, 2-furanyl, 3-furanyl, 2-thienyl, 3-thienyl, 2-oxazolyl, 2-thiazolyl, 4-isoxazolyl, 2-imidazolyl, pyrazolyl, triazolyl, 1,3-dioxolanyl, and 1,3-dioxanyl.

In another embodiment, the present invention provides that $R^2$ is selected from the group methyl substituted with 0–3 $R^{3f}$, $C_{1-3}$ alkyl substituted with 0–2 $R^4$, $C_{2-3}$ alkenyl substituted with 0–2 $R^4$, $C_{2-3}$ alkynyl substituted with 0–1 $R^4$, and $C_{3-6}$ cycloalkyl substituted with 0–2 $R^{3d}$.

In another embodiment, the present invention provides that $R^2$ is selected from the group methyl substituted with 0–3 $R^{3f}$, $C_{1-3}$ alkyl substituted with 1 $R^4$, $C_{2-3}$ alkenyl substituted with 1 $R^4$, and $C_{2-3}$ alkynyl substituted with 1 $R^4$.

In another embodiment, the present invention provides that $R^2$ is selected from the group methyl substituted with 0–2 $R^{3f}$, methyl substituted with 0–2 $R^4$, ethyl substituted with 0–2 $R^4$, propyl substituted with 0–2 $R^4$, ethenyl substituted with 0–2 $R^4$, 1-propenyl substituted with 0–2 $R^4$, 2-propenyl substituted with 0–2 $R^4$, ethynyl substituted with 0–2 $R^4$, 1-propynyl substituted with 0–2 $R^4$, 2-propynyl substituted with 0–2 $R^4$, and cyclopropyl substituted with 0–1 $R^{3d}$.

In another embodiment, the present invention provides that $R^2$ is selected from the group methyl substituted with 0–2 $R^{3f}$, methyl substituted with 0–2 $R^4$, ethyl substituted with 0–2 $R^4$, propyl substituted with 0–1 $R^4$, ethenyl substituted with 0–2 $R^4$, 1-propenyl substituted with 0–2 $R^4$, 2-propenyl substituted with 0–2 $R^4$, ethynyl substituted with 0–2 $R^4$, 1-propynyl substituted with 0–2 $R^4$.

In another embodiment, $R^2$ is selected from the group methyl substituted with 0–2 $R^{3f}$, methyl substituted with 0–2 $R^4$, and ethyl substituted with 0–2 $R^4$.

In another embodiment, the present invention provides that $R^{3f}$, at each occurrence, is independently selected from the group H, F, Cl, Br, I, $C_{1-4}$ alkyl, CN, —OH, —O—$R^{11}$, —O(CO)—$R^{13}$, —$SR^{11}$, —S(O)$R^{11}$, —S(O)$_2R^{11}$, and —$NR^{12}R^{12a}$.

In another embodiment, the present invention provides that $R^{3f}$, at each occurrence, is independently selected from the group H, F, Cl, Br, I, $C_{1-4}$ alkyl, —OH, CN, —O—$R^{11}$, —O(CO)—$R^{13}$, and —$NR^{12}R^{12a}$, —$SR^{11}$, —S(O)$R^{11}$, S(O)$_2 R^{11}$, and —OS(O)$_2$methyl.

In another embodiment, the present invention provides that $R^{3f}$, at each occurrence, is independently selected from the group H, F, Cl, Br, I, $C_{1-4}$ alkyl, CN, —OH, —O—$R^{11}$, —$SR^{11}$, —S(O)$R^{11}$, —S(O)$_2R^{11}$, and —$NR^{12}R^{12a}$.

In another embodiment, the present invention provides that $R^{3f}$, at each occurrence, is independently selected from the group H, F, Cl, Br, I, and —O—$R^{11}$.

In another embodiment, the present invention provides that $R^4$ is selected from the group H, Cl, F, $C_{1-4}$ alkyl substituted with 0–2 $R^{3e}$, $C_{3-6}$ carbocycle substituted with 0–2 $R^{3e}$, phenyl substituted with 0–5 $R^{3e}$, and a 5–6 membered heterocyclic system containing 1–3 heteroatoms selected from the group O, N, and S, substituted with 0–2 $R^{3e}$.

In another embodiment, the present invention provides that $R^4$ is selected from the group H, Cl, F, $C_{1-4}$ alkyl substituted with 0–1 $R^{3e}$, $C_{3-5}$ carbocycle substituted with 0–2 $R^{3e}$, phenyl substituted with 0–2 $R^{3e}$, and a 5–6 membered heterocyclic system containing 1–3 heteroatoms selected from the group O, N, and S, substituted with 0–1 $R^{3e}$, wherein the heterocyclic system is selected from 2-pyridyl, 3-pyridyl, 4-pyridyl, 2-furanyl, 3-furanyl, 2-thienyl, 3-thienyl, 2-oxazolyl, 2-thiazolyl, 4-isoxazolyl, 2-imidazolyl, pyrazolyl, triazolyl, 1,3-dioxolanyl, and 1,3-dioxanyl.

In another embodiment, the present invention provides that $R^4$ is selected from the group H, Cl, F, $CH_3$, $CH_2CH_3$, cyclopropyl substituted with 0–1 $R^{3e}$, 1-methyl-cyclopropyl substituted with 0–1 $R^{3e}$, cyclobutyl substituted with 0–1 $R^{3e}$, phenyl substituted with 0–2 $R^{3e}$, and a 5–6 membered heterocyclic system containing 1–3 heteroatoms selected from the group O, N, and S, substituted with 0–1 $R^{3e}$, wherein the heterocyclic system is selected from the group 2-pyridyl, 3-pyridyl, 4-pyridyl, 2-imidazolyl, pyrazolyl, triazolyl, 1,3-dioxolanyl, and 1,3-dioxanyl.

In another embodiment, the present invention provides that $R^4$ is selected from the group H, Cl, F, $CH_3$, $CH_2CH_3$, cyclopropyl substituted with 0–1 $R^{3e}$, 1-methyl-cyclopropyl substituted with 0–1 $R^{3e}$, cyclobutyl substituted with 0–1 $R^{3e}$, phenyl substituted with 0–2 $R^{3e}$, and a 5–6 membered heterocyclic system containing 1–3 heteroatoms selected from the group O, N, and S, substituted with 0–1 $R^{3e}$, wherein the heterocyclic system is selected from the group 2-pyridyl, 3-pyridyl, 4-pyridyl, 2-imidazolyl, pyrazolyl, triazolyl, 1,3-dioxolanyl, and 1,3-dioxanyl.

In another embodiment, the present invention provides that $R^8$ is H.

In another embodiment, the present invention provides that $R^9$ is selected from H, methyl, ethyl, propyl, and i-propyl.

In another embodiment, the present invention provides that $R^9$ is H.

In another embodiment, the present invention provides that $R^{11}$ is selected from methyl, ethyl, propyl, i-propyl, butyl, i-butyl, t-butyl, and $C_{3-6}$ carbocycle substituted with 0–2 $R^{3e}$ wherein the $C_{3-6}$ carbocycle is selected from cyclopropyl, cyclobutyl, cyclopentyl, cyclohexyl and phenyl.

In another embodiment, the present invention provides that $R^{12}$ and $R^{12a}$ are independently selected from H, methyl, ethyl, propyl, i-propyl, butyl, i-butyl, t-butyl, and $C_{3-6}$ carbocycle substituted with 0–2 $R^{3e}$ wherein the $C_{3-6}$ carbocycle is selected from cyclopropyl, cyclobutyl, cyclopentyl, cyclohexyl and phenyl.

In another embodiment, the present invention provides that W is $CR^3$; X is $CR^{3a}$; Y is $CR^{3b}$; and Z is $CR^{3c}$.

In another embodiment, the present invention provides that W is CH; X is $CR^{3a}$; Y is CH; and Z is CH.

In another embodiment, the present invention provides that W is $CR^3$; X is $CR^{3a}$; Y is $CR^{3b}$; and Z is N or $CR^{3c}$.

In another embodiment, the present invention provides that W is $CR^3$; X is $CR^{3a}$; Y is N or $CR^{3b}$; and Z is N or $CR^{3c}$.

In another embodiment, the present invention provides that W is $CR^3$; X is N or $CR^{3a}$; Y is $CR^{3b}$; and Z is N or $CR^{3c}$.

In another embodiment, the present invention provides that W is N or $CR^3$; X is $CR^{3a}$; Y is $CR^{3b}$; and Z is N or $CR^{3c}$.

The invention may be embodied in other specific forms without departing from the spirit or essential attributes thereof. This invention also encompasses all combinations of aspects of the invention noted herein. It is understood that any and all embodiments of the present invention may be taken in conjunction with any other embodiment to describe additional embodiments of the present invention. Furthermore, any elements of an embodiment are meant to be combined with any and all other elements from any of the embodiments to describe additional embodiments.

DEFINITIONS

It will be appreciated that the compounds of the present invention contain an asymmetrically substituted carbon atom, and may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated. All tautomers of shown or described compounds are also considered to be part of the present invention.

As used herein, the term "tricyclic 2-pyrimidones" is intended to include the compounds 5,10-dihydropyrimido [5,4-b]quinolin-4(3H)-one which are represented by the compounds of Formula I.

The present invention is intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

The term "substituted," as used herein, means that any one or more hydrogens on the designated atom or ring is replaced with a selection from the indicated group, provided that the atom's, or the ring atom's, normal valency is not exceeded, and that the substitution results in a stable compound. When a substituent is keto (i.e., =O), then 2 hydrogens on the atom are replaced. When a ring system (e.g., carbocyclic or heterocyclic) is said to be substituted with a carbonyl group or a double bond, it is intended that the carbonyl group or double bond be part (i.e., within) of the ring.

When any variable (e.g., $R^e$) occurs more than one time in any constituent or formula for a compound, its definition at each occurrence is independent of its definition at every other occurrence. Thus, for example, if a group is shown to be substituted with 0–2 $R^4$, then said group may optionally be substituted with up to two $R^4$ groups and $R^4$ at each occurrence is selected independently from the definition of $R^4$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, the following terms and expressions have the indicated meanings.

As used herein, "alkyl" is intended to include both branched and straight-chain saturated aliphatic hydrocarbon groups having the specified number of carbon atoms. By way of illustration, the term "$C_{1-10}$, alkyl" or "$C_1$–$C_{10}$ alkyl" is intended to include $C_1$, $C_2$, $C_3$, $C_4$, $C_5$, $C_6$, $C_7$, $C_8$, $C_9$, and $C_{10}$ alkyl groups. "$C_{1-4}$ alkyl" is intended to include $C_1$, $C_2$, $C_3$, and $C_4$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-10}$ alkoxy, is intended to include $C_1$, $C_2$, $C_3$, $C_4$, $C_5$, $C_6$, $C_7$, $C_8$, $C_9$, and $C_{10}$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl, is intended to include $C_3$, $C_4$, $C_5$, $C_6$, and $C_7$ cycloalkyl groups. "Alkenyl" is intended to include hydrocarbon chains of either a straight or branched configuration and one or more unsaturated carbon—carbon bonds which may occur in any stable point along the chain, such as ethenyl, propenyl and the like. $C_{2-10}$ alkenyl, is intended to include $C_2$, $C_3$, $C_4$, $C_5$, $C_6$, $C_7$, $C_8$, $C_9$, and $C_{10}$ alkenyl groups. "Alkynyl" is intended to include hydrocarbon chains of either a straight or branched configuration and one or more triple carbon—carbon bonds which may occur in any stable point along the chain, such as ethynyl, propynyl and the like. $C_{2-10}$ alkynyl, is intended to include $C_2$, $C_3$, $C_4$, $C_5$, $C_6$, $C_7$, $C_8$, $C_9$, and $C_{10}$ alkynyl groups.

"Halo" or "halogen" as used herein refers to fluoro, chloro, bromo and iodo. "Counterion" is used to represent a small, negatively charged species such as chloride, bromide, hydroxide, acetate, sulfate and the like.

As used herein, "aryl" or "aromatic residue" is intended to mean an aromatic moiety containing the specified number of carbon atoms, such as phenyl or naphthyl. As used herein, "carbocycle" or "carbocyclic residue" is intended to mean any stable 3, 4, 5, 6, or 7-membered monocyclic or bicyclic or 7, 8, 9, 10, 11, 12 or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2] bicyclooctane, fluorenyl, phenyl, naphthyl, indanyl, adamantyl, or tetrahydronaphthyl.

As used herein, the term "heterocycle" or "heterocyclic system" is intended to mean a stable 5, 6, or 7-membered monocyclic or bicyclic or 7, 8, 9, or 10-membered bicyclic heterocyclic ring which is saturated partially unsaturated or unsaturated (aromatic), and which consists of carbon atoms and 1, 2, 3, or 4 heteroatoms independently selected from the group consisting of N, O and S and including any bicyclic group in which any of the above-defined heterocyclic rings is fused to a benzene ring. The nitrogen and sulfur heteroatoms may optionally be oxidized. An oxo group may be a substituent on a nitrogen heteroatom to form an N-oxide. The heterocyclic ring may be attached to its pendant group at any heteroatom or carbon atom that results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heteroatoms independently selected from the group consisting of N, O and S. It is preferred that the total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 1,3-dioxolanyl, 1,3-dioxanyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

As used herein, "HIV reverse transcriptase inhibitor" is intended to refer to both nucleoside and non-nucleoside inhibitors of HIV reverse transcriptase (RT). Examples of nucleoside RT inhibitors include, but are not limited to, AZT, ddC, ddI, d4T, PMPA, and 3TC. Examples of non-nucleoside RT inhibitors include, but are no limited to, delavirdine (Pharmacia and Upjohn U90152S), efavirenz (DuPont), nevirapine (Boehringer Ingelheim), trovirdine (Lilly), MKC-442 (Triangle), HBY 097 (Hoechst), HBY1293 (Hoechst), GW867 (Glaxo Wellcome), ACT (Korean Research Institute), UC-781 (Rega Institute), UC-782 (Rega Institute), RD4-2025 (Tosoh Co. Ltd.), MEN 10979 (Menarini Farmaceutici) AG1549 (S1153; Agouron), TMC-120, TMC-125, and Calanolide A.

As used herein, "HIV protease inhibitor" is intended to refer to compounds that inhibit HIV protease. Examples include, but are not limited, saquinavir (Roche, Ro3-8959), ritonavir (Abbott, ABT-538), indinavir (Merck, MK-639), amprenavir (Vertex/Glaxo Wellcome), nelfinavir (Agouron, AG-1343), palinavir (Boehringer Ingelheim), BMS-232623 (Bristol-Myers Squibb), GS3333 (Gilead Sciences), KNI-413 (Japan Energy), KNI-272 (Japan Energy), LG-71350 (LG Chemical), CGP-61755 (Ciba-Geigy), PD 173606 (Parke Davis), PD 177298 (Parke Davis), PD 178390 (Parke Davis), PD 178392 (Parke Davis), U-140690 (Pharmacia and Upjohn), tipranavir (Pharmacia and Upjohn, U-140690), DMP-450 (DuPont), AG-1776, VX-175, MK-944, VX-478 and ABT-378. Additional examples include the cyclic protease inhibitors disclosed in WO93/07128, WO 94/19329, WO 94/22840, and PCT Application Number US96/03426.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carbbxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention. Examples of prodrugs at $R^8$ and at $R^9$ are $C_{1-6}$ alkylcarbonyl, $C_{1-6}$ alkoxy, $C_{1-4}$ alkoxycarbonyl, $C_{6-10}$ aryloxy, $C_{6-10}$ aryloxycarbonyl, $C_{6-10}$ arylmethylcarbonyl, $C_{1-4}$ alkylcarbonyloxy $C_{1-4}$ alkoxycarbonyl, $C_{6-10}$ arylcarbonyloxy $C_{1-4}$ alkoxycarbonyl, $C_{1-6}$ alkylaminocarbonyl, phenylaminocarbonyl, and phenyl $C_{1-4}$ alkoxycarbonyl.

"Stable compound" and "stable structure" are meant to indicate a compound that is sufficiently robust to survive isolation to a useful degree of purity from a reaction mixture, and formulation into an efficacious therapeutic agent. Only stable compounds are contemplated by the present invention.

"Therapeutically effective amount" is intended to include an amount of a compound of the present invention alone or an amount of the combination of compounds claimed or an amount of a compound of the present invention in combination with other active ingredients effective to inhibit HIV infection or treat the symptoms of HIV infection in a host. The combination of compounds may be a synergistic combination. Synergy, as described for example by Chou and Talalay, Adv. Enzyme Regul. 22:27–55 (1984), occurs when the effect (in this case, inhibition of HIV replication) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Other features of the invention will become apparent in the course of the following descriptions of exemplary embodiments that are given for illustration of the invention and are not intended to be limiting thereof.

SYNTHESIS

The compounds of Formula I can be prepared using the reactions and techniques described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991).

Co-pending U.S. patent application Ser. No. 09/691,249 filed Oct. 18, 2000 and Ser. No. 09/908,995, filed Jul. 19, 2001, which are hereby incorporated by reference, describes the synthesis of tricyclic compounds.

SCHEME 1

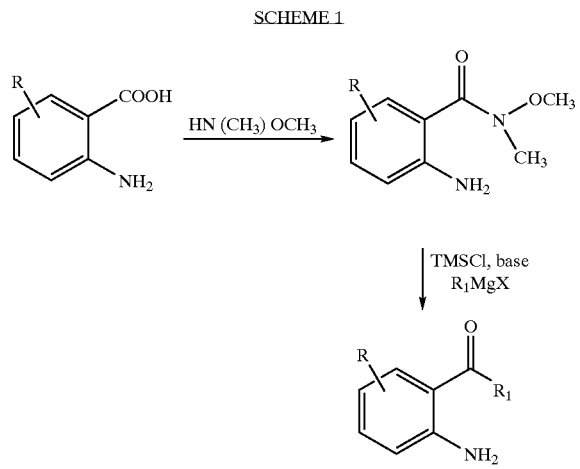

Scheme 1 illustrates a method of preparing keto-anilines from an appropriately substituted 2-aminobenzoic acid (wherein R represents $R^3$, $R^{3a}$, $R^{3b}$, and $R^{3c}$). The acid is converted to its N-methoxy-N-methyl amide derivative which can then be displaced to obtain the $R^1$-substituted ketone. The keto-anilines are useful intermediates for the presently claimed compounds.

SCHEME 2

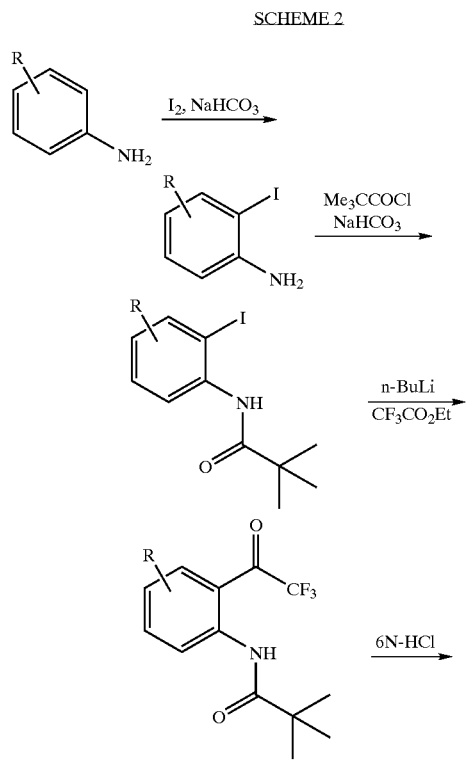

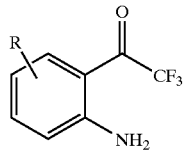

Scheme 2 describes another method of preparing keto-anilines, this time from an appropriately substituted aniline. After iodination and amine protection, a group such as trifluoromethyl can be introduced using a strong base and ethyl trifluoroacetate. Deprotection provides the keto-aniline. Additional means of preparing keto-anilines are known to one of skill in the art, e.g, Houpis et al, *Tetr. Lett.* 1994, 35(37), 6811–6814, the contents of which are hereby incorporated herein by reference.

SCHEME 3

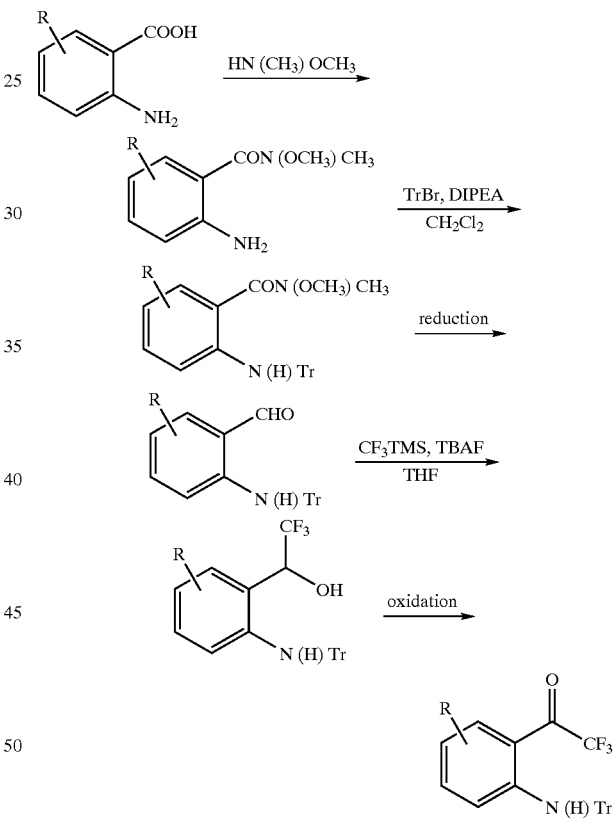

Another method of making 2-trifluoroacetylanilines is shown in Scheme 3. After forming the protected aniline, the amide is then reduced and the trifluoromethyl group added. Oxidation with an oxidant, such as $MnO_2$, provides the useful intermediate.

While the above schemes describe methods of preparing the benzo analogs (i.e. wherein W, X, Y, and Z are all carbon), they can be modified by one skilled in the art to prepare the heterocyclic varieties wherein W, X, Y, or Z are equal to nitrogen.

SCHEME 4

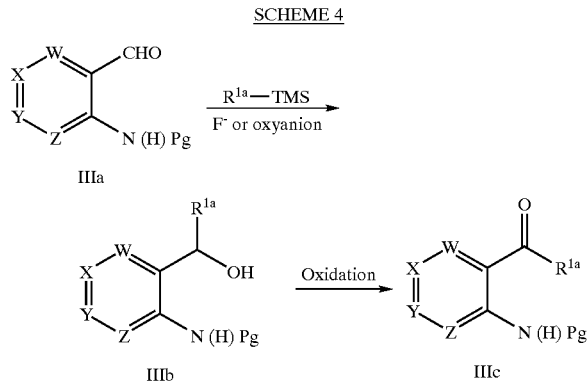

Scheme 4 illustrates specific steps for forming the aminoketone IIIc. Intermediate IIIb ($R^{1a}$ is selected from $CF_3$, $CF_3CF_2$, and $CF_3CF_2CF_2$) is useful for making some of the presently claimed compounds. Pg is an amine protecting group as defined previously, for example trityl (triphenylmethyl). The protected or unprotected aminobenzaldehyde, preferably protected, is treated with a perfluoroalkyl trimethylsilane, preferably trifluoromethyl trimethylsilane, followed by fluoride anion, such as tetrabutylammonium fluoride. In the same fashion, $CF_3CF_2TMS$, $CF_3CF_2CF_2TMS$ can also be used to prepare the appropriately substituted ketones. Other sources of fluoride anion such as sodium fluoride, potassium fluoride, lithium fluoride, cesium fluoride as well as oxyanionic species such as potassium tert-butoxide, sodium methoxide, sodium ethoxide and sodium trimethylsilanolate can also be used. Aprotic solvents such as DMF and THF can be used, preferably THF. The amount of perfluoroalkyl trimethylsilane used can be from about 1 to about 3 equivalents with an equivalent amount of fluoride anion or oxyanionic species. The reaction can be typically carried out at temperatures between about –20° C. to about 50° C., or about –10 to about 10° C., or about 0° C.

Conversion of IIIb to IIIc can be achieved by using an oxidizing agent well known to one of skill in the art such as $MnO_2$, PDC, PCC, $K_2Cr_2O_7$, $CrO_3$, $KMnO_4$, $BaMnO_4$, $Pb(OAc)_4$, and $RuO_4$. A preferred oxidant is $MnO_2$. Such conversion can be performed in an aprotic solvent like THF, DMF, dichloromethane dichloroethane, or tetrachloroethane, preferably dichloromethane.

SCHEME 5

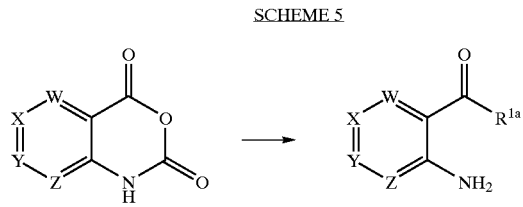

In addition to the methods of obtaining keto-anilines described in Schemes 1 and 2, nucleophilic opening of isatoic anhydrides can also be used as shown in Scheme 5. This reaction is accomplished by using an anionic nucleophile of the group $R^{1a}$. See Mack et al, *J. Heterocyclic Chem.* 1987, 24, 1733–1739; Coppola et al, *J. Org. Chem.* 1976, 41 (6), 825–831; Takimoto et al, *Fukuoka Univ. Sci. Reports* 1985, 15 (1), 37–38; Kadin et al, *Synthesis* 1977, 500–501; Staiger et al, *J. Org. Chem.* 1959, 24, 1214–1219.

The stoichiometry of the isatoic anhydride reagent to nucleophile is about 1.0 to 2.1 molar equivalents. The use of 1.0 eq. or more (e.g., 1.1, 1.2, 1.3, 1.4, 1.5, 1.6, 1.7, 1.8, 1.9, or 2.0) of anion (or anion precursor) is used to force the conversion and improve the isolated yield. The temperature used is from –20 to +35° C., such as temperatures below 0° C. being, or at –20° C. Reactions are run to about completion with time dependent upon inter alia nucleophile, solvent, and temperature. The nucleophilic addition is run in THF, for example, but any aprotic solvent would be suitable. Reaction with the active nucleophilic anion is the only criterion for exclusion of a solvent.

Patent Publications WO98/14436, WO98/45276, and WO01/29037 describe other methods of preparing the appropriately substituted anilines and are hereby incorporated by reference.

The resulting keto-anilines described in the above schemes can be modified to the compounds of the present invention using the schemes described in the examples.

One enantiomer of a compound of Formula I may display superior activity compared with the other. Thus, both of the following stereochemistries are considered to be a part of the present invention.

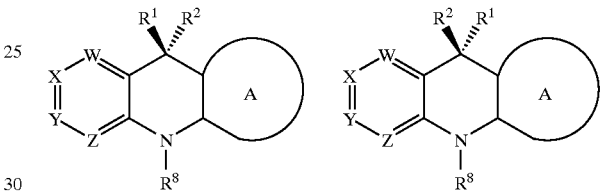

When required, separation of the racemic material can be achieved by HPLC using a chiral column or by a resolution using a resolving agent such as camphonic chloride as in Steven D. Young, et al, *Antimicrobial Agents and Chemotheraphy*, 1995, 2602–2605.

Other features of the invention will become apparent in the course of the following descriptions of exemplary embodiments that are given for illustration of the invention and are not intended to be limiting thereof.

EXAMPLES

Abbreviations used in the Examples are defined as follows: "° C." for degrees Celsius, "d" for doublet, "dd" for doublet of doublets, "eq" for equivalent or equivalents, "g" for gram or grams, "mg" for milligram or milligrams, "mL" for milliliter or milliliters, "H" for hydrogen or hydrogens, "hr" for hour or hours, "m" for multiplet, "M" for molar, "min" for minute or minutes, "MHz" for megahertz, "MS" for mass spectroscopy, "nmr" or "NMR" for nuclear magnetic resonance spectroscopy, "t" for triplet, "TLC" for thin layer chromatography, "ACN" for acetic anhydride, "CDI" for carbonyl diimidazole, "DIEA" for diisopropylethylamine, "DIPEA" for diisopropylethylamine, "DMAP" for dimethylaminopyridine, "DME" for dimethoxyethane, "EDAC" for 1-(3-dimethylaminopropyl)-3-ethylcarbodiimide hydrochloride, "LAH" for lithium aluminium hydride, "TBAF" for tetrabutylammonium fluoride, "TBS-Cl" for t-butyldimethylsilyl chloride, and "TEA" for triethylamine.

All reactions were run under a nitrogen atmosphere at room temperature and most were not optimized. The reactions were followed by TLC. Reactions run over night were done so for adequate time. Reagents were used as received. Dimethylformamide, tetrahydrofuran and acetonitrile were dried over molecular sieves. All other solvents were reagent grade. Ethanol and methanol were absolute and water was deionized. Melting points were determined in open capillary tubes on a Mel-Temp apparatus and are uncorrected. Column chromatographies were done on flash silica gel. Exceptions to any of the conditions above are noted in the text. Ciral HPLC separations were done using chiral columns which gave the enantiomers in >99% EE.

The following methods are illustrated in the synthethic schemes that follow the methods. While the schemes are described for specific compounds, the same methods were employed to synthesize the other compounds that are listed in the table of examples.

Example 1

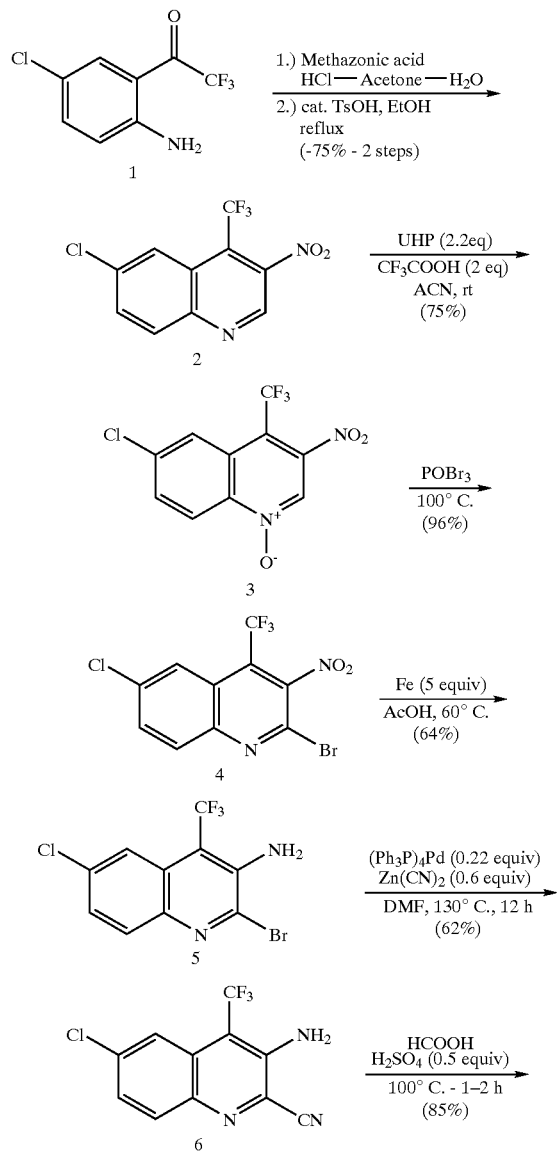

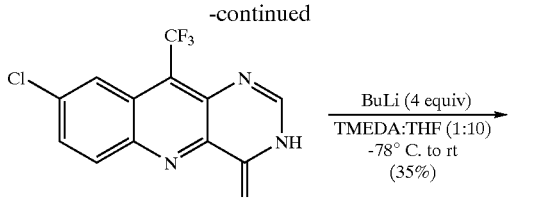

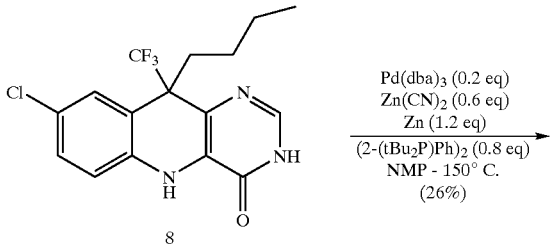

6-Chloro-3-nitro-4-(trifluoromethyl)quinoline (2): Preparation of Methazonic acid: To a stirred solution of NaOH (10.74 g, 179 mmol) in H$_2$O (60 mL) was added CH$_3$NO$_2$ dropwise maintaing the temperature between 45–50° C. Once the addition was complete, the reaction was cooled to 0° C. and the pH was adjusted to 1 by the slow addition of conc. HCl with care to keep the temperature below 10° C.

The solution of methazonic acid was poured into a stirred rt solution of 2-amino-5-chloro-trifluoromethylacetophenone in H$_2$O-acetone-HCl (200-120-24 mL). After approximately 20 minutes a yellow precipitate began to form. The reaction mixture was stirred overnight at rt and the precipitate (12.08 g) collected by filtration. The yellow solid was treated with p-TsOH.H$_2$O in EtOH (100 mL) and heated to reflux for 1 h. The reaction was cooled at rt and the solvent reduced in half by rotary evaporation. The yellow crystalline solid was collected by filtrated and washed with cold EtOH to afford 2 (9.41 g, 76%, two steps). mp 107–110° C., (needles, EtOH). R$_f$ 0.33 (5% Ethyl acetate-hexane). $^1$H NMR (d$_6$-DMSO, 300 MHz) δ 9.53 (s, 1H), 8.38 (d, J=9.1 Hz, 1H), 8.22 (m, 1H), 8.18 (dd, J=9.1, 2.2 Hz, 1H); $^{13}$C NMR (d$_6$-DMSO, 75 MHz) δ 147.54, 144.63, 136.42, 134.00, 132.94, 123.94, 122.11, 97.46, 94.72, 83.79; $^{19}$F NMR (d$_6$-DMSO, 300 MHz) δ −56.46; IR (KBr) υ$_{max}$ 1608, 1543, 1495, 1376, 1362, 1300, 1289, 1259, 1252, 1214, 1174, 1164, 1147, 1128, 1094, 848, 818, 664, 649 cm$^{-1}$.

Anal. Calcd for C$_{10}$H$_4$ClF$_3$N$_2$O$_2$: C, 43.42; H, 1.46; N, 10.13. Found: C, 43.47; H, 1.47; N, 9.90.

6-Chloro-3-nitro-4-(trifluoromethyl)quinoline 1-oxide (3): A mixture of 2 (22.89 g, 83 mmol) and urea-hydrogen peroxide complex (15.6 g, 166 mmol, 2 equiv) were suspended in CH$_3$CN (420 mL) and cooled to 0° C. Trifluoroacetic anhydride (24.5 mL, 174 mmol, 2.1 equiv) was added slowly keeping the temperature below 7° C. The reaction was stirred at 0° C. for 1 h then warmed to rt and stirred for an additional hour at which point the reaction was complete by TLC. The reaction mixture was quenched by the addition of 250 mL of NaHSO$_3$ and then poured into 0.5 N HCl (600 mL). The aqueous phase was extracted with 3×150 mL of EtOAc. The combined organics were washed with brine, dried over MgSO$_4$, and concentrated. Recrystallization of the resulting solid from EtOH afforded the desired product as a light tan crystalline solid (17.3 g, 71%). mp 130° C. R$_f$ 0.30 (10% Ethyl acetate-hexane). $^1$H NMR (CDCl$_3$, 300 MHz) δ 8.73 (d, J=9.3 Hz, 1H), 8.54 (s, 1H), 8.26 (m, 1H), 7.88 (dd, J=2.0, 9.3 Hz, 1H); $^{19}$F NMR (CDCl$_3$, 300 MHz) δ −55.91; $^{13}$C NMR (CDCl$_3$, 75 MHz) δ 141.74, 139.21, 133.54, 128.90, 125.67, 125.61, 123.01, 122.12, 119.37; IR (KBr) υ$_{max}$ 3104, 1584, 1558, 1498, 1360, 1324, 1284, 1249, 1178, 1160, 1137, 1128, 839 cm$^{-1}$.

Anal. Calcd for C$_{10}$H$_4$ClF$_3$N$_2$O$_3$: C, 41.05; H, 1.38; N, 9.57. Found: C, 41.02; H, 1.43; N, 9.48.

2-Bromo-6-chloro-3-nitro-4-(trifluoromethyl)quinoline (4): A mixture of 3 (4.71 g, 16.1 mmol) and POBr$_3$ (9.23 g, 32.2 mmol) were heated to 100° C. After 2 h, the reaction was cooled to rt and partitioned between EtOAc and H$_2$O, adding ice when necessary. The mixture was stirred overnight to break up the solid materials. Et$_2$O (100 mL) was added and the organic phase was removed. The remaining aqueous phase was extracted with EtOAc (3×100 mL). The combined organic phases were washed with brine, dried over MgSO$_4$ and concentrated to afford 5.5 g (96%) of the desired product which was used without further purification. An analytically pure sample was obtained by recrystallization (EtOH) to provide a fluffy off-white solid, mp 120° C. R$_f$ 0.61 (10% Ethyl acetate-hexane). $^1$H NMR (CDCl$_3$, 300 MHz) δ 8.16 (d, J=9.1 Hz, 1H), 8.16 (m, 1H), 7.92 (dd, J=2.2, 9.1 Hz, 1H); $^{19}$F NMR (CDCl$_3$, 300 MHz) δ −57.63; $^{13}$C NMR (CDCl$_3$, 75 MHz) δ 146.50, 137.35, 134.25, 131.88, 131.32, 124.45, 124.40, 122.44, 121.96, 118.76; IR (KBr) υ$_{max}$ 1606, 1588, 1552, 1492, 1426, 1382, 1361, 1308, 1283, 1219, 1180, 1169, 1157, 1134, 1097, 1023, 960, 846, 823, 792, 693, 661, 632 cm$^{-1}$.

Anal. Calcd for C$_{10}$H$_3$BrClF$_3$N$_2$O$_2$: C, 33.79; H, 0.851; N, 7.88. Found: C, 33.60; H, 1.06; N, 7.49.

Alternatively, the above reaction can be run using the following procedure: POBr$_3$ (39.2 g, 137 mmol, 2 equiv) was added to a stirred solution of 3 (20 g, 68 mmol) in dichloroethane (150 mL). The reaction was heated to reflux for 8 h. After cooling to rt, the reaction was quenched by the slow addition of ice. (Here I let it stir over the weekend—but not necessary). The organic layer was separated and the aqueous layer was extracted with CHCl$_3$ (2×100 mL). The combined organic layer was washed with NaHCO$_3$ (1×150 mL), H$_2$O (1×150 mL), NaHSO$_3$ (1×150 mL), H$_2$O (1×150 mL), brine (1×150 mL) and dried over MgSO$_4$. The residue was recrystallized from EtOH to afford the desired product, 16.12 g (67%). An additional 1.87 g was obtained by column chromatography of the concentrated filtrate (SiO$_2$, 5% ethyl acetate-hexane). Total yield 17.99 g (74%).

2-Bromo-6-chloro-4-(trifluoromethyl)quinolinamine (5): 2-Bromo-6-chloro-3-nitro-4-(trifluoromethyl)-quinoline (4, 4.5 g, 12.7 mmol) was suspended in AcOH (120 mL). Fe powder (3.5 g, 63.3 mmol) was added and the reaction was stirred under N$_2$ at 60° C. for 2 h. The AcOH was removed by rotary evaporation and the residue was partitioned between EtOAc (100 mL) and H$_2$O (100 mL). The biphasic mixture was sonicated for 30 s and then filtered through celite. The organic phase was washed with H$_2$O (1×75 mL), 1N aq. NaOH soln. (1×75 mL), H$_2$O (1×75 mL) and brine (1×50 mL), then dried over MgSO$_4$. Silica Chromatography (SiO$_2$, 65 mm×13 cm, 10% EtOAc-hexane) provided 5 as an off-white crystalline solid (2.30 g, 56%). mp 118° C. R$_f$ 0.4 (10% Ethyl acetate-hexane). $^1$H NMR (CDCl$_3$, 300 MHz) δ 7.90 (m, 1H), 7.85 (d, J=8.8 Hz, 1H), 7.44 (dd, J=2.2, 8.7 Hz, 1H), 5.37 (br s, 2H, NH$_2$); $^{19}$F NMR (CDCl$_3$, 300 MHz) δ −54.5; $^{13}$C NMR (CDCl$_3$, 75 MHz) δ 139.42, 136.87, 136.72, 135.20, 130.60, 127.26, 126.78, 125.47, 123.13, 121.87, 121.81; IR (KBr) υ$_{max}$ 3550, 3412, 1615, 1604, 1339, 1302, 1211, 1148, 1120, 1097, 1037, 974, 818 cm$^{-1}$.

Anal. Calcd for C$_{10}$H$_5$BrClF$_3$N$_2$: C, 36.90; H, 1.55; N, 8.61. Found: C, 37.10; H, 1.86; N, 8.46.

2-Bromo-6-chloro-4-(trifluoromethyl) quinolinecarbonitrile (6): 2-Bromo-6-chloro-4-(trifluoromethyl)-quinolineamine (5, 476 mg, 1.46 mmol) was dissolved in anhydrous DMF (5 mL) under N$_2$. Zn(CN)$_2$ (103 mg, 0.88 mmol) was added and the solution was degassed with a stream of N$_2$. Pd(PPh$_3$)$_4$ (34 mg, 0.029 mmol) was added and the solution was degassed again and then heated to 140° C. The reaction was complete by TLC after 80 min. The reaction mixture was cooled to rt and diluted with EtOAc (100 mL), The organic phase was washed with H$_2$O (2×20 mL) and brine (1×20 mL) then dried over MgSO$_4$. Concentration and chromatography (SiO$_2$, 40 g, 10% EtOAc-hexane) provided the desired material 6 as a yellow crystalline solid (202 mg, 51%). mp 188° C. R$_f$ 0.34 (10% Ethyl acetate-hexane). $^1$H NMR (CDCl$_3$, 300 MHz) δ 7.95 (d, J=8.8 Hz, 1H), 7.94 (m, 1H), 7.52 (dd, J=2.2, 8.8 Hz, 1H), 5.34 (br s, 2H, NH$_2$); $^{19}$F NMR (CDCl$_3$, 300 MHz) δ −54.51; $^{13}$C NMR (CDCl$_3$, 75 MHz) δ 140.21, 139.00, 138.39, 132.27, 128.25, 126.65, 126.10, 122.98, 121.90, 121.84, 114.43; IR (KBr) υ$_{max}$ 3485, 3410, 3386, 2230, 1650, 1639, 1574, 1492, 1430, 1352, 1322, 1221, 1158, 1130, 1121, 1095, 975, 822 cm$^{-1}$.

Anal. Calcd for C$_{11}$H$_5$ClF$_3$N$_3$: C, 48.64; H, 1.86; N, 15.47. Found: C, 48.71; H, 1.77; N, 15.27.

Alternatively, the above reaction can be run at 110° C., for 5–6 h to give 15.6 g, 95% yield.

8-Chloro-10-(trifluoromethyl)pyrimido[5,4-b]quinolin-4 (3H)-one (7): 2-Bromo-6-chloro-4-(trifluoromethyl)-quinolinecarbonitrile (6, 150 mg, 0.552 mmol) was suspended in formic acid (1.8 mL). Sulfuric acid (2 drops) was added and the reddish suspension was heated to 100° C. After 2h, no starting material remained by TLC. The reaction was cooled to ~60° C. and diluted with H$_2$O. The precipitate was collected, washed with H$_2$O and air-dried to provide 7 as a pale yellow solid (140.5 mg, 85%) requiring no further purification. $^1$H NMR (d$_6$-DMSO, 300 MHz) δ 12.8 (br s, NH), 8.39 (d, J=9.1 Hz, 1 H), 8.33 (m, 1H), 8.31 (s, 1H), 8.01 (dd, J=2.2, 9.1 Hz, 1H); $^{19}$F NMR (CDCl$_3$, 300 MHz) δ −51.35.

10-Butyl-8-chloro-10-(trifluoromethyl)-5,10-dihydropyrimido[5,4-b]quinolin-4(3H)-one (8): 8-Chloro-10-(trifluoromethyl)pyrimido[5,4-b]quinolin-4(3H)-one (7, 87 mg, 0.290 mmol) was suspended in anhydrous THF-TMEDA (10:1, 2 mL) and cooled to −78° C. under a nitrogen atmosphere. n-BuLi (1.6M 0.73 mL, 4 equiv) was added dropwise over 10 minutes. After the addition was complete, the reaction was stirred for 20 minutes at −78° C. and then warmed to rt over 45 minutes. The reaction was quenched with sat. NH$_4$Cl solution and then partitioned between H$_2$O and EtOAc. The aqueous layer was extracted with EtOAc (2×) and Et$_2$O (2×). The combined organic phases were dried over Na$_2$SO$_4$ and concentrated. Chromatography (SiO$_2$, 50% EtOAc-hexane) afforded the desired material 8 as a tan solid (35.4 mg, 34%). R$_f$ 0.34 (50% Ethyl acetate-hexane). $^1$H NMR (CDCl$_3$, 300 MHz) δ 11.42 (br s, NH), 7.78 (s, 1H), 7.30 (m, 1H), 7.18 (dd, J=2.2, 8.5 Hz, 1H), 6.95 (br s, NH), 6.77 (d, J=8.5 Hz, 1H), 2.75 (m, 1H); 2.12 (m, 1H), 1.28 (m, 2H), .0.95 (m, 2H), 0.79 (t, J=7.4 Hz, 3H). ESI-HRMS 358.0935 (M$^+$+H, $C_{16}H_{15}ClON_3F_3$ requires 358.0934).

Example 2

10-Butyl-8-cyano-10-(trifluoromethyl)-5,10-dihydropyrimido[5,4-b]quinolin-4(3H)-one (9): 10-Butyl-8-chloro-10-(trifluoromethyl)-5,10-dihydropyrimido[5,4-b]quinolin-4(3H)-one (8, 34 mg, 0.095 mmol) was dissolved in NMP (0.5 mL, 0.2M). Zn (7.4 mg, 0.114 mmol, 1.2 equiv), Zn(CN)$_2$ (6.7 mg, 0.057 mmol, 0.6 equiv) and 2-(di-t-butylphosphino)biphenyl (23 mg, 0.076 mmol, 0.8 equiv) were added and the solution was degassed with a stream of nitrogen. Pd$_2$(dba)$_3$ (17 mg, 0.019 mmol, 0.2 equiv) was added and the reaction was degassed a second time before heating to 150° C. After 16 hours, the reaction was complete by TLC. The reaction was cooled to rt and diluted with EtOAc (0.7 mL). The organic phase was washed with 2N aq. NH$_4$OH solution, brine and then concentrated with a stream of N$_2$. Chromatography (SiO$_2$, 15% acetone-CH$_2$Cl$_2$, then 50% EtOAc-hexane) provided the desired material as a beige solid (8.7 mg, 26%). R$_f$ 0.27 (50% Ethyl acetate-hexane). $^1$H NMR (CDCl$_3$, 300 MHz) 610.53 (br S, NH), 7.87 (s, 1H), 7.69 (s, 1H), 7.54 (d, J=8.5 Hz, 1H), 6.94 (d, J=8.5 Hz, 1H), 2.86 (m, 1H), 1.39 (m, 2H), 0.99 (m, 2H), 0.86 (t, J=7.3 Hz, 3H). $^{19}$F NMR (CDCl$_3$, 300 MHz) δ −75.62; ESI-HRMS 349.1295 (M$^+$+H, $C_{17}H_{15}F_3N_4O$ requires 349.1276).

Example 3

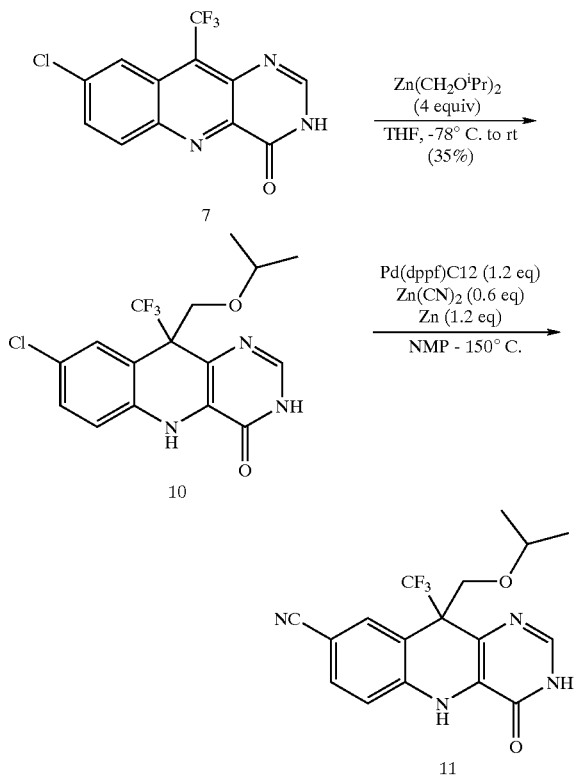

8-Chloro-10-(isopropoxymethyl)-10-(trifluoromethyl)-5,10-dihydropyrimido[5,4-b]quinolin-4(3H)-one (10): Tri-n-butyl-isopropoxymethyl-stannane (19 mL, 47.2 mmol) was dissolved in anhydrous THF (50 mL) under N$_2$ and cooled to −78° C. n-BuLi (1.6 M in THF, 29.5 mL, 47.2 mmol) was added and the reaction mixture was stirred for 15 min before the addition of ZnCl$_2$ (0.5 M in THF, 47.2 mL, 23.6 mmol). The reaction was allowed to warm slowly to rt and was stirred for 2 h. The zinc mixture was transferred via cannula to a solution of 8-Chloro-10-(trifluoromethyl)pyrimido[5,4-b]quinolin-4(3H)-one (7, 2.47 g, 7.87 mmol) in THF (100 mL). The reaction mixture was stirred overnight at room temperature. After quenching with sat. aq. NH$_4$Cl, the reaction mixture was partitioned between EtOAc and H$_2$O. The organic phase was washed with H$_2$O (1×), dried over Na$_2$SO$_4$, and concentrated. Chromatography (SiO$_2$, 50% EtOAc-hexane) afforded the desired material as a white solid (696 mg, 24%). R$_f$ 0.35 (50% Ethyl acetate-hexane). $^1$H NMR (d$_6$-acetone, 300 MHz) δ 11.47 (br s, NH), 8.30 (br s, NH), 7.88 (s, 1H), 7.35 (d, J=8.7 Hz, 1H), 7.27 (dd, J=2.3, 8.7 Hz, 1H), 4.68 (d, J=9.0 Hz, 1H), 4.34 (d, J=9.0 Hz, 1H), 3.66 (m, 1H), 1.03 (d, J=6.1 Hz, 1H), 0.97 (d, J=6.1 Hz, 1H); $^{19}$F NMR (d$_6$-acetone, 300 MHz) δ −73.83; ESI-HRMS 374.0905(M$^+$+H, $C_{16}H_{15}ClF_3N_3O_2$ requires 374.0883).

Example 4

8-Cyano-10-(isopropoxymethyl)-10-(trifluoromethyl)-5,10-dihydropyrimido[5,4-b]quinolin-4(3H)-one (11): 8-Chloro-10-(isopropoxymethyl)-10-(trifluoromethyl)-5,10-dihydropyrimido[5,4-b]quinolin-4(3H)-one (10, 696 mg, 1.86 mmol) was dissolved in anhydrous NMP (15 mL). Zn powder (268 mg, 4.10 mmol) and Zn(CN)$_2$ (437 mg, 3.72 mmol) were added and the reaction mixture was degassed under vacuum (3×). Pd(dppf)Cl$_2$.CH$_2$Cl$_2$ (1.67 g, 2.05 mmol) was added and the reaction was degassed again under vacuum (3×). After heating to 170° C. for 16 hours, the reaction was cooled to rt and partitioned between EtOAc and 1N NH$_4$OH solution. The biphasic mixture was filtered through celite and the aqueous phase was removed. The organic phase was washed with H$_2$O (2×), dried over MgSO4 and concentrated. The dark brown oil was redissolved in NMP (15 mL) and subjected to the identical reaction conditions for a second time. After workup, the dark brown oil was obtained. Flash chromatography (SiO$_2$, 50% EtOAc-hexane) followed by PTLC (30% Acetone-hexane) afforded the desired material as a yellow solid (80 mg, 12%). R$_f$ 0.29 (50% Ethyl acetate-hexane). $^1$H NMR (d$_6$-acetone, 300 MHz) δ 11.62 (br s, NH), 8.76 (br s, NH), 7.97 (s, 1H), 7.96 (s, 1H), 7.62 (dd, J=1.9, 8.5 Hz, 1H), 7.48 (d, J=8.5 Hz, 1H), 4.72 (d, J=9.0 Hz, 1H), 4.41 (d, J=9.0 Hz, 1H), 3.68 (m, 1H), 1.03 (d, J=6.1 Hz, 3H), 0.98 (d, J=6.1 Hz, 3H); $^{19}$F NMR (d$_6$-acetone, 300 MHz) δ −74.11; ESI-HRMS 365.1223 (M$^+$+H, $C_{17}H_{15}F_3N_4O$ requires 365.1225).

8-Cyano-10-(isopropoxymethyl)-10-(trifluoromethyl)-5,10-dihydropyrimido[5,4-b]quinolin-4(3H)-one (11) was separated into enantiomers by chiral HPLC.

Example 5

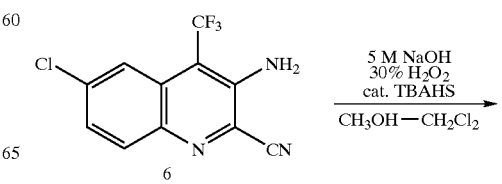

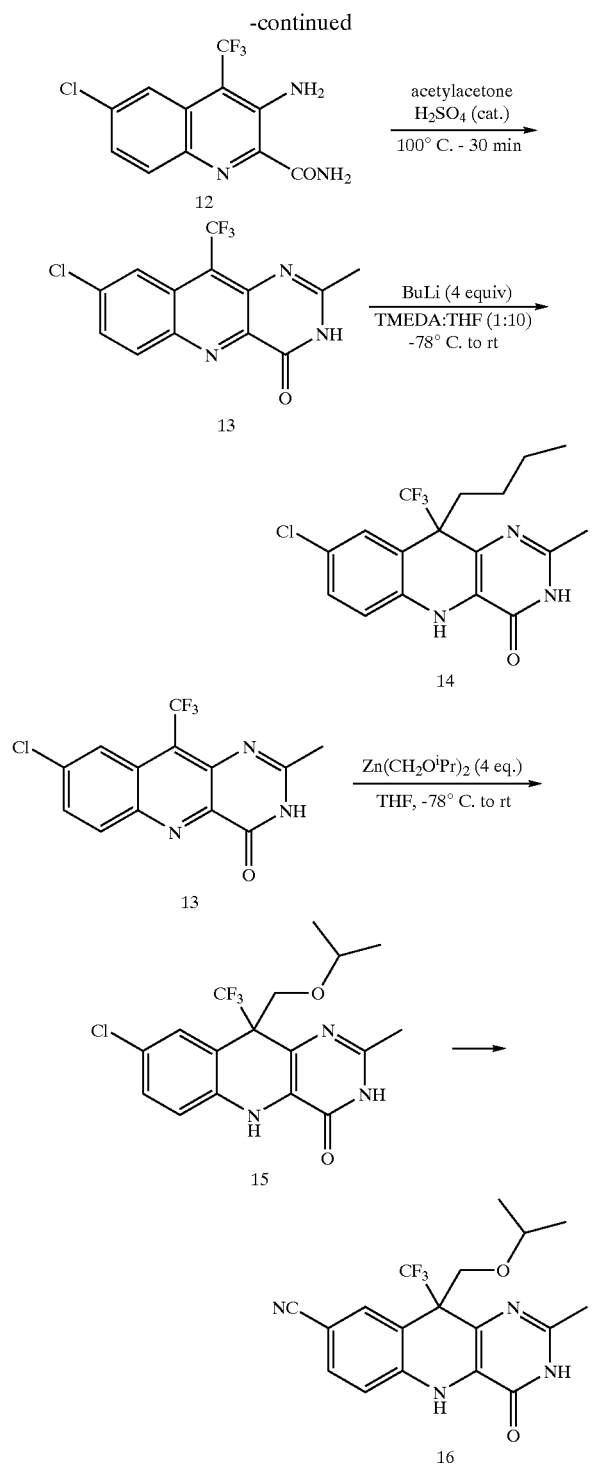

the solids. The reaction was allow to warm to rt and stir overnight. The reaction mixture was partitioned between EtOAc (25 mL) and H$_2$O (25 mL), and the aqueous layer was extracted with EtOAc (3×15 mL). The combined organic phases were washed with brine, dried (MgSO$_4$) and concetrated. Chromatography (SiO$_2$, 40 g, 30% EtOAc-hexane) afforded the desired product as a yellow crystalline solid (183 mg, 65%). mp 200° C. R$_f$ 0.37 (10% EtOAc-hexane). $^1$H NMR (CDCl$_3$, 300 MHz) δ 8.20 (br s, NH$_2$), 7.91 (m, 1H), 7.83 (d, J=8.8 Hz, 1H), 7.40 (dd, J=2.2, 9.0 Hz, 1H), 5.63 (br s, NH$_2$); $^{19}$F NMR (CDCl$_3$, 300 MHz) δ −54.42; $^{13}$C NMR (CDCl$_3$, 75 MHz) δ 168.75, 141.64, 137.05, 136.90, 135.87, 131.96, 128.07, 126.59, 123.84, 121.45, 121.38; IR (KBr) υ$_{max}$ 3515, 3447, 3268, 3204, 1690, 1674, 1597, 1586, 1438, 1357, 1315, 1303, 1226, 1109, 974, 822, 750 cm$^{-1}$.

Anal. Calcd for C$_{11}$H$_7$ClF$_3$N$_3$O: C, 45.62 H, 2.44; N, 14.51. Found: C, 45.73; H, 2.34; N, 14.18.

8-Chloro-2-methyl-10-(trifluoromethyl)-pyrimido[5,4-b]quinolin-4(3H)-one (13): 3-Amino-6-chloro-4-(trifluoromethyl)-2-quinolinecarboxamide (12, 172 mg, 0.594 mmol) was dissolved acetylacetone (5.9 mL). Three drops of H$_2$SO$_4$ were added and the reaction was heated to 100° C. for 30 minutes. The reaction was cooled to rt and the copious cream precipitate was collected and washed with cold CH$_3$OH to provide the desired product (103 mg, 55%) requiring no further purification. $^1$H NMR (d$_6$-DMSO, 300 MHz) δ 12.73 (br s, NH), 8.35 (d, J=9.2 Hz, 1 H), 8.29 (s, 1H), 7.97 (dd, J=2.2, 9.1 Hz, 1H), 2.44 (s, 3H); $^{19}$F NMR (CDCl$_3$, 300 MHz) δ −51.34; IR (KBr) υ$_{max}$ 3442, 3060, 2920, 1706, 1629, 1608, 1560, 1485, 1336, 1329, 1198, 1144, 1114, 961, 837, 710 cm$^{-1}$.

10-Butyl-8-chloro-2-methyl-10-(trifluoromethyl)-5,10-dihydropyrimido[5,4-b]quinolin-4(3H)-one (14): 8-Chloro-2-methyl-10-(trifluoromethyl)-pyrimido[5,4-b]quinolin-4 (3H)-one (13, 82 mg, 0.261 mmol) was suspended in THF-TMEDA (10:1, 1.74 mL) and cooled to −78° C. under a N$_2$ atmosphere. n-BuLi was added dropwise and the reaction slowly became homogeneous. The reaction mixture was stirred at −78° C. for 20 minutes, then the ice bath was removed and the reaction allowed to warm to rt. After stirring for 90 min, the reaction was quenched with sat. aq. NH$_4$Cl and was partitioned between EtOAc and H$_2$O. The organic layer was separated and the aqueous layer was extracted with EtOAc (3×10 mL). The combined organics were washed with brine, dried over Na$_2$SO$_4$ and concentrated. Chromatography (SiO$_2$, 60% EtOAc-hexane) provided the desired material 14 (17 mg, 17%). R$_f$ 0.39 (50% EtOAc-hexane). $^1$H NMR (CDCl$_3$, 300 MHz) δ 11.63 (br s, NH), 7.53 (s, 1H), 7.22 (dd, J=2.2, 8.4 Hz, 1H), 6.87 (br s, NH), 6.82 (d, J=8.4 Hz, 1H), 2.86 (m, 1H), 2.48 (s, 3H), 2.14 (m, 1H), 1.34 (m, 2H), 1.01 (m, 2H), 0.86 (t, J=7.3 Hz, 3H); $^{19}$F NMR (CDCl$_3$, 300 MHz) δ −75.21. ESI-HRMS 372.1099 (M$^+$+H, C$_{17}$H$_{17}$ClON$_3$F$_3$ requires 372.1091).

3-Amino-6-chloro-4-(trifluoromethyl)-2-quinolinecarboxamide (12): 10-Butyl-8-cyano-10-(trifluoromethyl)-5,10-dihydropyrimido[5,4-b]quinolin-4 (3H)-one (9, 264 mg, 0.972 mmol) was dissolved in CH$_3$OH—CH$_2$Cl$_2$ (1:2, 6.5 mL) and treated with tetrabutylammonium hydrogen sulfate (109 mg, 0.321 mmol) and 30% aq. H$_2$O$_2$ (1.98 mL). The reaction was cooled to 0° C. and 5N aq. NaOH solution (5.8 mL) was added. After the addition was complete, the reaction mixture had solidified. Additional CH$_3$OH—CH$_2$Cl$_2$ (6 mL) was added to dissolve Example 6

8-Chloro-10-(isopropoxymethyl)-2-methyl-10-(trifluoromethyl)-5,10-dihydropyrimido[5,4-b]quinolin-4 (3H)-one (15): Tri-n-butyl-isopropoxymethyl-stannane (0.774 mL, 1.92 mmol) was dissolved in anhydrous THF (2 mL) under N$_2$ and cooled to −78° C. n-BuLi (1.6 M in THF, 1.2 mL, 1.92 mmol) was added and the reaction mixture was stirred for 15 min before the addition of ZnCl$_2$ (0.5 M in THF, 1.92 mL, 0.96 mmol). The reaction was allowed to warm slowly to rt and was stirred for 90 min. The zinc mixture was transferred via cannula to a solution of 8-Chloro-2-methyl-10-(trifluoromethyl)pyrimido[5,4-b]quinolin-4(3H)-one (13, 99 mg, 0.32 mmol) in THF (4 mL). The reaction mixture was stirred overnight at room temperature. After quenching with sat. aq. NH$_4$Cl, the reaction mixture was partitioned between EtOAc and H$_2$O. The organic phase was washed with H$_2$O (1×), dried over Na$_2$SO$_4$, and concentrated. Chromatography (PTLC, SiO$_2$, 50% EtOAc-hexane) afforded the desired material as a white solid (25 mg, 20%). R$_f$ 0.37 (50% EtOAc-hexane). $^1$H NMR (acetone-d$_6$, 300 MHz) δ 11.15 (br s, NH), 8.23 (s, 1H), 7.55 (s, 1H), 7.31 (d, J=8.7 Hz, 1H), 7.24 (dd, J=2.2, 8.7 Hz, 1H), 4.71 (d, J=8.9 Hz, 1H), 4.31 (d, J=8.9 Hz, 1H), 2.86 (m, 1H), 3.66 (m, 1H), 2.38 (s, 3H), 1.02 (d, J=6.1 Hz, 3H), 0.99 (d, J=6.1 Hz, 3H); $^{19}$F NMR (acetone-d$_6$, 300 MHz) δ −73.73. ESI HRMS m/z 388.1040 (M$^+$+H, C$_{17}$H$_{17}$ClF$_3$N$_3$O$_2$ requires 388.1040)

Example 7

8-Cyano-10-(isopropoxymethyl)-2-methyl-10-(trifluoromethyl)-5,10-dihydropyrimido[5,4-b]quinolin-4(3H)-one (16): 8-Chloro-10-(isopropoxymethyl)-2-methyl-10-(trifluoromethyl)-5,10-dihydropyrimido[5,4-b]quinolin-4(3H)-one (15, 4.45 g, 11.47 mmol) was dissolved in anhydrous NMP (70 mL). Zn powder (900 mg, 13.76 mmol) and Zn(CN)$_2$ (2.69 g, 22.94 mmol) were added and the reaction mixture was degassed under vacuum (3×). [(t-Bu)$_3$P]$_2$ Pd (4.79 g, 9.18 mmol) was added and the reaction was degassed again under vacuum (3×). After heating to 170° C. for 16 hours, the reaction was cooled to rt and most of the NMP was removed by vacuum distillation at 60° C. The cooled residue was diluted with EtOAc and filtered through celite to provide a yellow oil. Flash chromatography (SiO$_2$, 10% Acetone-CH$_2$Cl$_2$) provided an oil which was partiioned between EtOAc and H$_2$O. The organic layer was washed with H$_2$O (1×) to removed any residual NMP, dried over MgSO$_4$ and concentrated. Trituration of the resulting solid with CH$_2$Cl$_2$ provided the desired material as a white powder (3.56 g, 82%). mp 277.3–278.1° C. (decomp). R$_f$ 0.21 (50% EtOAc-hexane). $^1$H NMR (acetone-PH-7410 NP 300 MHz) δ 11.51 (br s, NH), 8.59 (s, 1H), 7.95 (s, 1H), 7.59 (dd, J=1.8, 8.4 Hz, 1H), 7.43 (d, J=8.4 Hz, 1H), 4.74 (d, J=9.0 Hz, 1H), 4.38 (d, J=9.0 Hz, 1H), 3.68 (m, 1H), 2.40 (s, 3H), 1.02 (d, J=5.9 Hz, 3H), 0.99 (d, J=6.2 Hz, 3H); $^{19}$F NMR (acetone-d$_6$, 300 MHz) δ −74.04; $^{13}$C NMR (acetone-d$_6$, 75 MHz) δ205.3, 156.4, 148.8, 142.7, 134.5, 132.2, 130.2, 127.6, 125.2, 123.8, 119.0, 116.3, 115.4, 103.1, 72.5, 64.5, 21.3, 21.1, 20.5; IR (KBr) υ$_{max}$ 3426, 2973, 2883, 2222, 1676, 1612, 1506, 1372, 1323, 1247, 1231, 1178, 1127, 1113, 1041, 987, 881, 837, 752 cm$^{-1}$. ESI HRMS m/z 379.1387 (M$^+$+H, C$_{18}$H$_{18}$F$_3$N$_4$O$_2$ requires 379.1382).

Example 8

8-Chloro-10-(2-cyclopropylethyl)-10-(trifluoromethyl)-5,10-dihydropyrimido[5,4-b]quinolin-4(3H)-one (17): To a stirred solution of 1-cyclopropyl-2-iodoethane (12.5g, 63.9 mmol, 5 equiv) in anhydrous Et$_2$O (128 mL) at −78° C. was added tert-butyl lithium (1.7M in pentane, 75 mL, 128 mmol, 10 equiv). The resulting white suspension was stirred at −78° C. for 50 min and added via cannula to a suspension of 7 (3.83 g, 12.8 mmol) in THF (64 mL) at −78° C. The resulting dark yellow mixture was stirred at −78° C. for 30 min and then allowed to warm to 0° C. over 5 h. The reaction was quenched with satd. NH$_4$Cl (100 mL) and H$_2$O (100 mL). The reaction mixture was extracted with EtOAc (3×100 mL) and the combined organic layers washed with brine and dried (MgSO$_4$). Chromatography (SiO$_2$, 40 to 50% EtOAc-hexane) provided the desired product as a yellow solid (2.92 g, 62%). ESI HRMS m/z 370.1735 (M$^+$+H, C$_{17}$H$_{16}$ClF3N3O requires 370.0934).

Example 9

8-Cyano-10-(2-cyclopropylethyl)-10-(trifluoromethyl)-5,10-dihydropyrimido[5,4-b]quinolin-4(3H)-one (18): A mixture of 17 (110 mg, 0.297 mmol), Zn(CN)$_2$ (71 mg, 0.594 mmol, 2 equiv), [(t-Bu)$_3$P]$_2$ Pd (0.78 g, 0.149 mmol, 0.5 equiv) and Zn powder (29 mg, 0.446 mmol, 1.5 eq) were suspended in anhydrous NMP and degassed. The reaction mixture was heated to 170° C. for 30 h. After cooling to 25° C., the reaction was quenched with 2 N NH$_4$OH (20 mL) and extracted with EtOAc (2×25 mL). The combined organic phases were washed with brine, dried (MgSO$_4$) and concentrated. Chromatography (SiO$_2$, 50 to 60% EtOAc-hexane) afforded the desired product as an off-white solid (49 mg, 46%). mp >280° C. ESI HRMS m/z 361.1293 (M$^+$+H, C$_{18}$H$_{16}$F$_3$N$_4$O requires 361.1276).

Example 10

10-(4-Bromobenzyl)-8-chloro-10-(trifluoromethyl)-5,10-dihydropyrimido[5,4-b]quinolin-4(3H)-one (19): To a stirred suspension of 7 (200 mg, 0.667 mmol) in THF (4 mL) at −40° C. was added 4-bromobenzyl magnesium bromide (0.25 M in Et$_2$O, 13.3 mL, 3.34 mmol). The reaction was warmed slowly to 0° C. over 2 h. After stirring an additional 2 h, the reaction was quenched with H$_2$O (20 mL) and extracted with EtOAc (2×20 mL). The combined organic layers were washed with brine, dried (MgSO$_4$) and concentrated. Chromatography (SiO$_2$, 40 to 50% EtOAc-hexane) afforded the desired product as a viscous orange oil (134 mg, 43%). ESI-MS m/z 470.2 (M$^+$+H, C$_{19}$H$_{12}$BrClF$_3$N$_3$O).

The following compounds have been made using the techniques described above.

TABLE 1*

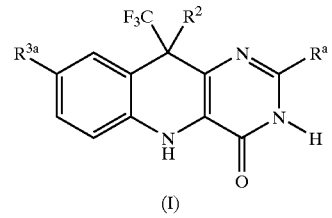

(I)

| Ex # | R$^a$ | R$^2$ | R$^{3a}$ | Mass Spec | MP (° C.) |
|---|---|---|---|---|---|
| 1 | H | n-butyl | Cl | 358.0935 | |
| 2 | H | n-butyl | CN | 349.1295 | |
| 3 | H | i-propoxymethyl | Cl | 374.0905 | |
| 4 | H | i-propoxymethyl | CN | 365.1223 | |
| 4a | H | i-propoxymethyl (R-configuration) | CN | | |
| 4b | H | i-propoxymethyl (S-configuration) | CN | | |
| 5 | CH$_3$ | n-butyl | Cl | 372.1099 | |
| 6 | CH$_3$ | i-propoxymethyl | Cl | 388.1040 | |
| 7 | CH$_3$ | i-propoxymethyl | CN | 379.1387 | |
| 8 | H | 2-cyclopropylethyl | Cl | 370.1735 | |
| 9 | H | 2-cyclopropylethyl | CN | 361.1293 | |
| 10 | H | 4-bromobenzyl | Cl | 470.2 | |

*Unless otherwise noted, stereochemistry is (+/−).

The following table contains representative examples of the present invention. Each entry in each table is intended to be paired with the formula at the start of the table. For example, in Table 2, the compound is intended to be paired with one of 1a–11a, one of 1b–4b, one of 1c–4c, one of 1d–5d and one of 1–60e.

TABLE 2

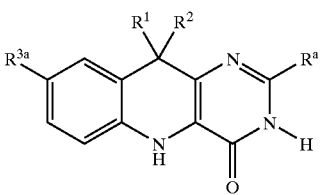

| # | $R^1$ |
|---|---|
| 1a | $CF_3$ |
| 2a | $CHF_2$ |
| 3a | $CH_3$ |
| 4a | cyclopropyl |
| 5a | $CF_2CF_3$ |
| 6a | methyl |
| 7a | ethyl |
| 8a | propyl |
| 9a | butyl |
| 10a | CN |
| 11a | hydroxymethyl |

| # | $R^{3a}$ |
|---|---|
| 1b | H |
| 2b | chloro |
| 3b | fluoro |
| 4b | $CH_3$ |
| 5b | CN |

| # | $R^a$ |
|---|---|
| 1c | chloro |
| 2c | methyl |
| 3c | H |

| # | $R^2$ |
|---|---|
| 1e | (6-methylpyrid-2-yl)methyl |
| 2e | Cyclopropylacetylenyl |
| 3e | n-Propyl |
| 4e | n-Butyl |
| 5e | 4-Fluorophenylmethyl |
| 6e | 2-Pyridylmethyl |
| 7e | i-Propyl |
| 8e | 3-Pyridylmethyl |
| 9e | 4-Pyridylmethyl |
| 10e | 3-Propynyl |
| 11e | 2-Pyridylethynyl |
| 12e | 2-(2-Pyridyl)ethyl |
| 13e | n-Propyl |
| 14e | 3-Propenyl |
| 15e | 2-Cyclopropylethyl |
| 16e | Ethynyl |
| 17e | 2-Ethoxyethyl |
| 18e | 2-chloroethyl |
| 19e | N-Cyclopropylaminomethyl |
| 20e | Hydroxymethyl |
| 21e | n-Propoxymethyl |
| 22e | i-Propoxymethyl |
| 23e | Methoxyethyl |
| 24e | diisopropoxymethyl |
| 25e | Propylaminomethyl |
| 26e | N-Methyl-i-propylaminomethyl |
| 27e | n-Propylaminomethyl |
| 28e | Cyclobutylaminomethyl |
| 29e | i-Butylaminomethyl |
| 30e | cyclopropylthiomethyl |
| 31e | i-propylsulfoxymethyl |
| 32e | t-butylsulfoxymethyl |
| 33e | methylthiomethyl |
| 34e | ethylthiomethyl |
| 35e | i-propylthiomethyl |

TABLE 2-continued

| 36e | cyclopropylmethoxymethyl |
|---|---|
| 37e | cyclobutoxymethyl |
| 38e | cyanomethyl |
| 39e | 2-(ethylamino)ethyl |
| 40e | 2-(dimethylamino)ethyl |
| 41e | 2-(methylamino)ethyl |
| 42e | 2-(i-propylamino)ethyl |
| 43e | 2-(cyclopropylamino)ethyl |
| 44e | pentyl |
| 45e | vinyl |
| 46e | imidazolylethyl |
| 47e | pyrazolylethyl |
| 48e | 1,2,4-triazolylethyl |
| 49e | 2-(methylethylamino)ethyl |
| 50e | 2-(i-propylethylamino)ethyl |
| 51e | 2-(pyrrolidinyl)ethyl |
| 52e | 3-pentanylaminomethyl |
| 53e | dimethoxymethyl |
| 54e | i-butylaminomethyl |
| 55e | cyclopropylmethyl aminomethyl |
| 56e | allylaminomethyl |
| 57e | (R)-sec-butylaminomethyl |
| 58e | (S)-sec-butylaminomethyl |
| 59e | 1,3-dioxolanylmethyl |
| 60e | 1,3-dioxanylmethyl |

UTILITY

The compounds of this invention possess reverse transcriptase inhibitory activity and HIV inhibitory efficacy. The compounds of formula (I) possess HIV reverse transcriptase inhibitory activity and are therefore useful as antiviral agents for the treatment of HIV infection and associated diseases. The compounds of formula (I) possess HIV reverse transcriptase inhibitory activity and are effective as inhibitors of HIV growth. The ability of the compounds of the present invention to inhibit viral growth or infectivity is demonstrated in standard assay of viral growth or infectivity, for example, using the assay described below.

The compounds of formula (I) of the present invention are also useful for the inhibition of HIV in an ex vivo sample containing HIV or expected to be exposed to HIV. Thus, the compounds of the present invention may be used to inhibit HIV present in a body fluid sample (for example, a serum or semen sample) that contains or is suspected to contain or be exposed to HIV.

The compounds provided by this invention are also useful as standard or reference compounds for use in tests or assays for determining the ability of an agent to inhibit viral replication and/or HIV reverse transcriptase, for example in a pharmaceutical research program. Thus, the compounds of the present invention may be used as a control or reference compound in such assays and as a quality control standard. The compounds of the present invention may be provided in a commercial kit or container for use as such standard or reference compound.

Since the compounds of the present invention exhibit specificity for HIV reverse transcriptase, the compounds of the present invention may also be useful as diagnostic reagents in diagnostic assays for the detection of HIV reverse transcriptase. Thus, inhibition of the reverse transcriptase activity in an assay (such as the assays described herein) by a compound of the present invention would be indicative of the presence of HIV reverse transcriptase and HIV virus.

As used herein "μg" denotes microgram, "mg" denotes milligram, "g" denotes gram, "μL" denotes microliter, "mL"

denotes milliliter, "L" denotes liter, "nM" denotes nanomolar, "μM" denotes micromolar, "mM" denotes millimolar, "M" denotes molar and "nm" denotes nanometer. "Sigma" stands for the Sigma-Aldrich Corp. of St. Louis, Mo.

Compounds tested in the assay described below are considered to be active if they exhibit a $K_i$ of $\leq 10$ μM. Other compounds of the present invention have $K_i$'s of $\leq 1$ μM. Other compounds of the present invention have $K_i$'s of $\leq 0.1$ μM. Other compounds of the present invention have $K_i$'s of $\leq 0.01$ μM. Other compounds of the present invention have $K_i$'s of $\leq 0.001$ μM.

Using the methodology described below, a number of compounds of the present invention were found to exhibit a $K_i$ of $\leq 10$ μM, thereby confirming the utility of the compounds of the present invention as effective HIV reverse transcriptase inhibitors.

HIV RNA Assay

DNA Plasmids and in Vitro RNA Transcripts:

Plasmid pDAB 72 containing both gag and pol sequences of BH10 (bp 113–1816) cloned into PTZ 19R was prepared according to Erickson-Viitanen et al. *AIDS Research and Human Retroviruses* 1989, 5, 577. The plasmid was linearized with Bam HI prior to the generation of in vitro RNA transcripts using the Riboprobe Gemini system II kit (Promega) with T7 RNA polymerase. Synthesized RNA was purified by treatment with RNase free DNAse (Promega), phenol-chloroform extraction, and ethanol precipitation. RNA transcripts were dissolved in water, and stored at −70° C. The concentration of RNA was determined from the $A_{260}$.

Probes:

Biotinylated capture probes were purified by HPLC after synthesis on an Applied Biosystems (Foster City, Calif.) DNA synthesizer by addition of biotin to the 5' terminal end of the oligonucleotide, using the biotin-phosphoramidite reagent of Cocuzza, *Tet. Lett.* 1989, 30, 6287. The gag biotinylated capture probe (as described in WO01/29037, published Apr. 26, 2001) was complementary to nucleotides 889–912 of HXB2 and the pol biotinylated capture probe (see WO01/29037) was complementary to nucleotides 2374–2395 of HXB2. Alkaline phosphatase conjugated oligonucleotides used as reporter probes were prepared by Syngene (San Diego, Calif.). The pol reporter probe (see WO01/29037) was complementary to nucleotides 2403–2425 of HXB2. The gag reporter probe (see WO01/29037) was complementary to nucleotides 950–973 of HXB2. All nucleotide positions are those of the GenBank Genetic Sequence Data Bank as accessed through the Genetics Computer Group Sequence Analysis Software Package (*Devereau Nucleic Acids Research* 1984, 12, 387). The reporter probes were prepared as 0.5 μM stocks in 2xSSC (0.3 M NaCl, 0.03 M sodium citrate), 0.05 M Tris pH 8.8, 1 mg/mL BSA. The biotinylated capture probes were prepared as 100 μM stocks in water.

Streptavidin Coated Plates:

Streptavidin coated plates were obtained from DuPont Biotechnology Systems (Boston, Mass.).

Cells and Virus Stocks:

MT-2 and MT-4 cells were maintained in RPMI 1640 supplemented with 5% fetal calf serum (FCS) for MT-2 cells or 10% FCS for MT-4 cells, 2 mM L-glutamine and 50 μg/mL gentamycin, all from Gibco. HIV-1 RF was propagated in MT-4 cells in the same medium. Virus stocks were prepared approximately 10 days after acute infection of MT-4 cells and stored as aliquots at −70° C. Infectious titers of HIV-1(RF) stocks were 1–3×10$^7$ PFU (plaque forming units)/mL as measured by plaque assay on MT-2 cells (see below). Each aliquot of virus stock used for infection was thawed only once.

For evaluation of antiviral efficacy, cells to be infected were subcultured one day prior to infection. On the day of infection, cells were resuspended at 5×10$^5$ cells/mL in RPMI 1640, 5% FCS for bulk infections or at 2×10$^6$/mL in Dulbecco's modified Eagles medium with 5% FCS for infection in microtiter plates. Virus was added and culture continued for 3 days at 37° C.

HIV RNA Assay:

Cell lysates or purified RNA in 3 M or 5 M GED were mixed with 5 M GED and capture probe to a final guanidinium isothiocyanate concentration of 3 M and a final biotin oligonucleotide concentration of 30 nM. Hybridization was carried out in sealed U bottom 96 well tissue culture plates (Nunc or Costar) for 16–20 hours at 37° C. RNA hybridization reactions were diluted three-fold with deionized water to a final guanidinium isothiocyanate concentration of 1 M and aliquots (150 μL) were transferred to streptavidin coated microtiter plates wells. Binding of capture probe and capture probe-RNA hybrid to the immobilized streptavidin was allowed to proceed for 2 hours at room temperature, after which the plates were washed 6 times with DuPont ELISA plate wash buffer (phosphate buffered saline(PBS), 0.05% Tween 20) A second hybridization of reporter probe to the immobilized complex of capture probe and hybridized target RNA was carried out in the washed streptavidin coated well by addition of 120 μl of a hybridization cocktail containing 4×SSC, 0.66% Triton× 100, 6.66% deionized formamide, 1 mg/mL BSA and 5 nM reporter probe. After hybridization for one hour at 37° C., the plate was again washed 6 times. Immobilized alkaline phosphatase activity was detected by addition of 100 μL of 0.2 mM 4-methylumbelliferyl phosphate (MUBP, JBL Scientific) in buffer (2.5 M diethanolamine pH 8.9 (JBL Scientific), 10 mM $MgCl_2$, 5 mM zinc acetate dihydrate and 5 mM N-hydroxyethyl-ethylene-diamine-triacetic acid). The plates were incubated at 37° C. Fluorescence at 450 nM was measured using a microplate fluorometer (Dynateck) exciting at 365 nM.

Microplate Based Compound Evaluation in HIV-1 Infected MT-2 Cells:

Compounds to be evaluated were dissolved in DMSO and diluted in culture medium to twice the highest concentration to be tested and a maximum DMSO concentration of 2%. Further three-fold serial dilutions of the compound in culture medium were performed directly in U bottom microtiter plates (Nunc). After compound dilution, MT-2 cells (50 μL) were added to a final concentration of 5×10$^5$ per mL (1×10$^5$ per well). Cells were incubated with compounds for 30 minutes at 37° C. in a $CO_2$ incubator. For evaluation of antiviral potency, an appropriate dilution of HIV-1 (RF) virus stock (50 μL) was added to culture wells containing cells and dilutions of the test compounds. The final volume in each well was 200 μL. Eight wells per plate were left uninfected with 50 μL of medium added in place of virus, while eight wells were infected in the absence of any antiviral compound. For evaluation of compound toxicity, parallel plates were cultured without virus infection.

After 3 days of culture at 37° C. in a humidified chamber inside a $CO_2$ incubator, all but 25 μL of medium/well was removed from the HIV infected plates. Thirty seven μL of 5 M GED containing biotinylated capture probe was added to the settled cells and remaining medium in each well to a final concentration of 3 M GED and 30 nM capture probe.

Hybridization of the capture probe to HIV RNA in the cell lysate was carried out in the same microplate well used for virus culture by sealing the plate with a plate sealer (Costar), and incubating for 16–20 hrs in a 37° C. incubator. Distilled water was then added to each well to dilute the hybridization reaction three-fold and 150 μL of this diluted mixture was transferred to a streptavidin coated microtiter plate. HIV RNA was quantitated as described above. A standard curve, prepared by adding known amounts of pDAB 72 in vitro RNA transcript to wells containing lysed uninfected cells, was run on each microtiter plate in order to determine the amount of viral RNA made during the infection.

In order to standardize the virus inoculum used in the evaluation of compounds for antiviral activity, dilutions of virus were selected which resulted in an $IC_{90}$ value (concentration of compound required to reduce the HIV RNA level by 90%) for dideoxycytidine (ddC) of 0.2 μg/mL. $IC_{90}$ values of other antiviral compounds, both more and less potent than ddC, were reproducible using several stocks of HIV-1 (RF) when this procedure was followed. This concentration of virus corresponded to ~3×10$^5$ PFU (measured by plaque assay on MT-2 cells) per assay well and typically produced approximately 75% of the maximum viral RNA level achievable at any virus inoculum. For the HIV RNA assay, $IC_{90}$ values were determined from the percent reduction of net signal (signal from infected cell samples minus signal from uninfected cell samples) in the RNA assay relative to the net signal from infected, untreated cells on the same culture plate (average of eight wells). Valid performance of individual infection and RNA assay tests was judged according to three criteria. It was required that the virus infection should result in an RNA assay signal equal to or greater than the signal generated from 2 ng of pDAB 72 in vitro RNA transcript. The $IC_{90}$ for ddC, determined in each assay run, should be between 0.1 and 0.3 μg/mL. Finally, the plateau level of viral RNA produced by an effective reverse transcriptase inhibitor should be less than 10% of the level achieved in an uninhibited infection. A compound was considered active if its $IC_{90}$ was found to be less than 20 μM.

For antiviral potency tests, all manipulations in microtiter plates, following the initial addition of 2×concentrated compound solution to a single row of wells, were performed using a Perkin Elmer/Cetus ProPette.

Protein Binding and Mutant Resistance

In order to characterize NNRTI compounds for their clinical efficacy potential the effect of plasma proteins on antiviral potency and measurements of antiviral potency against wild type and mutant variants of HIV that carry amino acid changes in the known binding site for NNRTIs were examined. The rationale for this testing strategy is two fold:

1. Many drugs are extensively bound to plasma proteins. Although the binding affinity for most drugs for the major components of human plasma, namely, human serum albumin (HSA) or alpha-1-acid glycoprotein (AAG), is low, these major components are present in high concentration in the blood. Only free or unbound drug is available to cross the infected cell membrane for interaction with the target site (i.e., HIV-1 reverse transcriptase, HIV-1 RT). Therefore, the effect of added HSA+AAG on the antiviral potency in tissue culture more closely reflects the potency of a given compound in the clinical setting. The concentration of compound required for 90% inhibition of virus replication as measured in a sensitive viral RNA-based detection method is designated the IC90. The fold increase in apparent IC90 for test compounds in the presence or added levels of HSA and AAG that reflect in vivo concentrations (45 mg/ml HSA, 1 mg/ml AAG) was then calculated. The lower the fold increase, the more compound will be available to interact with the target site.

2. The combination of the high rate of virus replication in the infected individual and the poor fidelity of the viral RT results in the production of a quasi-species or mixtures of HIV species in the infected individual. These species will include a majority wild type species, but also mutant variants of HIV and the proportion of a given mutant will reflect its relative fitness and replication rate. Because mutant variants including mutants with changes in the amino acid sequence of the viral RT likely pre-exist in the infected individual's quasi-species, the overall potency observed in the clinical setting will reflect the ability of a drug to inhibit not only wild type HIV-1, but mutant variants as well. We thus have constructed, in a known genetic background, mutant variants of HIV-1 that carry amino acid substitutions at positions thought to be involved in NNRTI binding, and measured the ability of test compounds to inhibit replication of these mutant viruses. The concentration of compound required for 90% inhibition of virus replication as measured in a sensitive viral RNA-based detection method is designated the IC90. It is desirable to have a compound which has high activity against a variety of mutants.

Dosage and Formulation

The antiviral compounds of this invention can be administered as treatment for viral infections by any means that produces contact of the active agent with the agent's site of action, i.e., the viral reverse transcriptase, in the body of a mammal. They can be administered by any conventional means available for use in conjunction with pharmaceuticals, either as individual therapeutic agents or in a combination of therapeutic agents. They can be administered alone, but preferably are administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to about 1000 milligrams per kilogram of body weight, with the preferred dose being about 0.1 to about 30 mg/kg.

Dosage forms of compositions suitable for administration contain from about 1 mg to about 100 mg of active ingredient per unit. In these pharmaceutical compositions the active ingredient will ordinarily be present in an amount of about 0.5–95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers are described in *Remington's Pharmaceutical Sciences, supra*, a standard reference text in this field.

Useful pharmaceutical dosage-forms for administration of the compounds of this invention can be illustrated as follows:

Capsules

A capsule formulation of the present invention can be prepared by filling standard two-piece hard gelatin capsules each with 100 mg of powdered active ingredient, 150 mg of lactose, 50 mg of cellulose, and 6 mg magnesium stearic.

Soft Gelatin Capsules

A soft gelatin capsule formulation of the present invention can be prepared as follows. A mixture of active ingredient in a digestible oil such as soybean oil, cottonseed oil or olive oil can be prepared and injected by means of a positive displacement pump into gelatin to form soft gelatin capsules containing 100 mg of the active ingredient. The capsules should then be washed and dried.

Tablets

A tablet formulation of the present invention can be prepared by conventional procedures so that the dosage unit is 100 mg of active ingredient, 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption.

Suspension

An aqueous suspension formulation can be prepared for oral administration so that each 5 mL contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral formulation suitable for administration by injection can be prepared by stirring 1.5% by weight of active ingredient in 10% by volume propylene glycol and water. The solution is sterilized by commonly used techniques.

Combination Administration of Therapeutic Agents

The present invention provides a method for the treatment of HIV infection which comprises administering, in combination, to a host in need thereof a therapeutically effective amount of the following:

(a) a compound of formula (I); and (b) at least one compound selected from the group consisting of HIV reverse transcriptase inhibitors and HIV protease inhibitors, in one or more sterile containers.

Each therapeutic agent component of this combination method (i.e., component (a) and (b) set forth above) can independently be administered in any separate dosage form, such as those described above, and can be administered in various ways, as described above. In the following description component (b) is to be understood to represent one or more agents as described previously. Each individual therapeutic agent comprising component (b) may also be independently be administered in any separate dosage form, such as those described above, and can be administered in various ways, as described above.

Components (a) and any one or more of the agents comprising component (b) of the combination method of the present invention may be formulated together, in a single dosage unit (that is, combined together in one capsule, tablet, powder, or liquid, etc.) as a combination product. When component (a) and (b) are not formulated together in a single dosage unit, the component (a) may be administered at the same time as component (b) or in any order; for example component (a) of this invention may be administered first, followed by administration of component (b), or they may be administered in the revserse order. If component (b) contains more that one agent, e.g., one RT inhibitor and one protease inhibitor, these agents may be administered together or in any order. When not administered at the same time, preferably the administration of component (a) and (b) occurs less than about one hour apart. Preferably, the route of administration of component (a) and (b) is oral. The terms oral agent, oral inhibitor, oral compound, or the like, as used herein, denote compounds which may be orally administered. Although it is preferable that component (a) and component (b) both be administered by the same route (that is, for example, both orally) or dosage form, if desired, they may each be administered by different routes or dosage forms (for example, one component of the combination method may be administered orally, and another component may be administered intravenously).

As is appreciated by a medical practitioner skilled in the art, the dosage of the combination therapy of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

The proper dosage of components (a) and (b) of the combination method of this invention will be readily ascertainable by a medical practitioner skilled in the art, based upon the present disclosure. By way of general guidance, typically a daily dosage may be about 100 milligrams to about 1.5 grams of each component. If component (b) represents more than one compound, then typically a daily dosage may be about 100 milligrams to about 1.5 grams of each agent of component (b). By way of general guidance, when the compounds of component (a) and component (b) are administered in combination, the dosage amount of each component may be reduced by about 70–80% relative to the usual dosage of the component when it is administered alone as a single agent for the treatment of HIV infection, in view of the synergistic effect of the combination.

The combination products of this invention may be formulated such that, although the active ingredients are combined in a single dosage unit, the physical contact between the active ingredients is minimized. In order to minimize contact, for example, where the product is orally administered, one active ingredient may be enteric coated.

By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose or other appropriate materials as known in the art, in order to further separate the active components. The polymer coating serves to form an additional barrier to interaction with the other component. In each formulation wherein contact is prevented between components (a) and (b) via a coating or some other material, contact may also be prevented between the individual agents of component (b).

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time or concurrently by the same manner, will be readily apparent to those skilled in the art, based on the present disclosure.

Pharmaceutical kits useful for the treatment of HIV infection, which comprise a therapeutically effective amount of a pharmaceutical composition comprising a compound of component (a) and one or more compounds of component (b), in one or more sterile containers, are also within the ambit of the present invention. Sterilization of the container may be carried out using conventional sterilization methodology well known to those skilled in the art. Component (a) and component (b) may be in the same sterile container or in separate sterile containers. The sterile containers of materials may comprise separate containers, or one or more multi-part containers, as desired. Component (a) and component (b) may be separate, or physically combined into a single dosage form or unit as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

As will be appreciated by one of skill in the art, numerous modifications and variations of the present invention are possible in light of the above teachings. It is therefore to be understood that within the scope of the appended claims, the invention may be practiced otherwise than as specifically described herein.

What is claimed is:

1. A compound of formula (I):

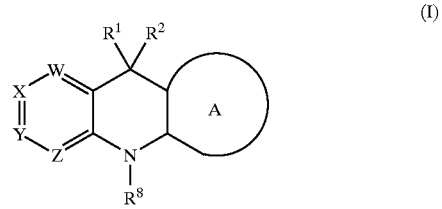

(I)

or a stereoisomeric form or mixture of stereoisomeric forms or a pharmaceutically acceptable salt form thereof, wherein:

A is a ring selected from:

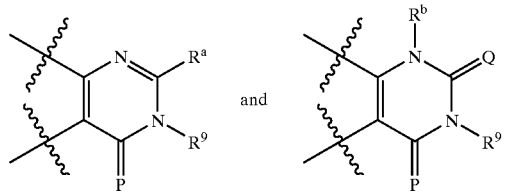

P is O or S;

Q is O or NH;

$R^a$ is selected from H, CN, $C_{1-4}$ alkyl, $C_{1-4}$ alkenyl, $C_{1-4}$ alkynyl, OH, $C_{1-4}$ alkyl-O—, $C_{1-4}$ alkyl-NH—, and $NH_2$;

$R^b$ is selected from H, $C_{1-4}$ alkyl, $C_{1-4}$ alkenyl, and $C_{1-4}$ alkynyl;

W is N or $CR^3$;

X is N or $CR^{3a}$;

Y is N or $CR^{3b}$;

Z is N or $CR^{3c}$;

provided that if two of W, X, Y, and Z are N, then the remaining are other than N;

$R^1$ is selected from the group cyclopropyl, hydroxymethyl, CN, and $C_{1-4}$ alkyl substituted with 0–9 halogen;

$R^2$ is selected from the group methyl substituted with 0–3 $R^{3f}$, $C_{1-6}$ alkyl substituted with 0–2 $R^4$, $C_{2-6}$ haloalkyl, $C_{2-5}$ alkenyl substituted with 0–2 $R^4$, $C_{2-5}$ alkynyl substituted with 0–1 $R^4$, $C_{3-6}$ cycloalkyl substituted with 0–2 $R^{3d}$, phenyl substituted with 0–2 $R^{3d}$, and 3–6 membered heterocyclic system containing 1–3 heteroatoms selected from the group O, N, and S, substituted with 0–2 $R^{3d}$;

$R^3$ is selected from the group H, $C_{1-4}$ alkyl, —OH, $C_{1-4}$ alkoxy, $OCF_3$, $CF_3$, F, Cl, Br, I, —$(CH_2)_rNR^5R^{5a}$, —NO$_2$, —CN, —C(O)R$^6$, —(CH$_2$)$_t$NHC(O)R$^7$, —(CH$_2$)$_t$NHC(O)NR$^5$R$^{5a}$, —NHSO$_2$R$^{10}$, —S—C$_{1-4}$ alkyl, —S(O)C$_{1-4}$alkyl, —S(O)$_2$C$_{1-4}$alkyl, —SO$_2$NR$^5$R$^{5a}$, and a 5–6 membered heteroaromatic ring containing 1–4 heteroatoms selected from the group O, N, and S;

R$^{3a}$ is selected from the group H, C$_{1-4}$ alkyl, —OH, C$_{1-4}$ alkoxy, OCF$_3$, CF$_3$, F, Cl, Br, I, —(CH$_2$)$_t$NR$^5$R$^{5a}$, —NO$_2$, —CN, —C(O)R$^6$, —(CH$_2$)$_t$NHC(O)R$^7$, —(CH$_2$)$_t$NHC(O)NR$^5$R$^{5a}$, —NHSO$_2$R$^{10}$, —S—C$_{1-4}$ alkyl, —S(O)C$_{1-4}$alkyl, —S(O)$_2$C$_{1-4}$alkyl, —SO$_2$NR$^5$R$^{5a}$, and a 5–6 membered heteroaromatic ring containing 1–4 heteroatoms selected from the group O, N, and S;

alternatively, R$^3$ and R$^{3a}$ together form —OCH$_2$O—;

R$^{3d}$ is selected from the group H, C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;

alternatively, R$^{3a}$ and R$^{3b}$ together form —OCH$_2$O—;

R$^{3c}$ is selected from the group H, C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;

alternatively, R$^{3b}$ and R$^{3c}$ together form —OCH$_2$O—;

R$^{3d}$, at each occurrence, is independently selected from the group H, C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;

R$^{3e}$, at each occurrence, is independently selected from the group H, C$_{1-4}$ alkyl, —OH, C$_{1-4}$ alkoxy, OCF$_3$, F, Cl, Br, I, —NR$^5$R$^{5a}$, —NO$_2$, —CN, —C(O)R$^6$, —NHC(O)R$^7$, —NHC(O)NR$^5$R$^{5a}$, —NHSO$_2$R$^{10}$, and —SO$_2$NR$^5$R$^{5a}$;

R$^{3f}$, at each occurrence, is independently selected from the group H, F, Cl, Br, I, C$_{1-4}$ alkyl, CN, —OH, —O—R$^{11}$, OCF$_3$, —O(CO)—R$^{13}$, —OS(O)$_2$C$_{1-4}$ alkyl, —NR$^{12}$R$^{12a}$, —C(O)R$^{13}$, —NHC(O)R$^{13}$, —SR$^{11}$, —S(O)R$^{11}$, —S(O)$_2$R$^{11}$, —NHSO$_2$R$^{10}$, and —SO$_2$NR$^{12}$R$^{12a}$;

R$^4$ is selected from the group H, F, Cl, Br, I, C$_{1-6}$ alkyl substituted with 0–2 R$^{3e}$, C$_{3-10}$ carbocycle substituted with 0–2 R$^{3e}$, phenyl substituted with 0–5 R$^{3e}$, and a 5–10 membered heterocyclic system containing 1–3 heteroatoms selected from the group O, N, and S, substituted with 0–2 R$^{3e}$;

R$^5$ and R$^{5a}$ are independently selected from the group H and C$_{1-4}$ alkyl;

alternatively, R$^5$ and R$^{5a}$, together with the nitrogen to which they are attached, combine to form a 5–6 membered ring containing 0–1 O or N atoms;

R$^6$ is selected from the group H, OH, C$_{1-4}$ alkyl, C$_{1-4}$ alkoxy, and NR$^5$R$^{5a}$;

R$^7$ is selected from the group H, C$_{1-3}$ alkyl and C$_{1-3}$ alkoxy;

R$^8$ is selected from the group H, (C$_{1-6}$ alkyl)carbonyl, C$_{1-6}$ alkoxy, (C$_{1-4}$ alkoxy)carbonyl, C$_{6-10}$ aryloxy, (C$_{6-10}$ aryl)oxycarbonyl, (C$_{6-10}$ aryl)methylcarbonyl, (C$_{1-4}$ alkyl)carbonyloxy(C$_{1-4}$ alkoxy)carbonyl, C$_{6-10}$ arylcarbonyloxy(C$_{1-4}$ alkoxy)carbonyl, C$_{1-6}$ alkylaminocarbonyl, phenylaminocarbonyl, phenyl (C$_{1-4}$ alkoxy)carbonyl, and NR$^5$R$^{5a}$(C$_{1-6}$ alkyl) carbonyl;

R$^9$ is selected from H, C$_{1-4}$ alkyl, C$_{1-4}$ alkenyl, C$_{1-4}$ alkynyl, (C$_{1-6}$ alkyl)carbonyl, C$_{1-6}$ alkoxy, (C$_{1-4}$ alkoxy)carbonyl, C$_{6-10}$ aryloxy, (C$_{6-10}$ aryl)oxycarbonyl, (C$_{6-10}$ aryl)methylcarbonyl, (C$_{1-4}$ alkyl) carbonyloxy(C$_{1-4}$ alkoxy)carbonyl, C$_{6-10}$ arylcarbonyloxy(C$_{1-4}$ alkoxy)carbonyl, C$_{1-6}$ alkylaminocarbonyl, phenylaminocarbonyl, phenyl (C$_{1-4}$ alkoxy)carbonyl, and NR$^5$R$^{5a}$(C$_{1-6}$ alkyl) carbonyl;

R$^{10}$ is selected from the group C$_{1-4}$ alkyl and phenyl;

R$^{11}$ is selected from C$_{1-6}$ alkyl, C$_{1-6}$ haloalkyl, C$_{1-6}$ alkyl substituted with C$_{3-6}$cycloalkyl substituted with 0–2 R$^{3e}$, C$_{2-6}$ alkenyl, C$_{2-6}$ alkynyl, C$_{3-6}$ carbocycle substituted with 0–2 R$^{3e}$;

R$^{12}$ and R$^{12a}$ are independently selected from H, C$_{1-6}$ alkyl, C$_{1-6}$ alkyl substituted with C$_{3-6}$cycloalkyl substituted with 0–2 R$^{3e}$, and C$_{3-6}$ carbocycle substituted with 0–2 R$^{3e}$;

alternatively, R$^{12}$ and R$^{12a}$ can join to form 4–7 membered heterocyclic ring;

R$^{13}$ is selected from the group H, C$_{1-6}$ alkyl, C$_{1-6}$ haloalkyl, C$_{1-6}$ alkoxy, C$_{2-6}$ alkenyl, C$_{2-6}$ alkynyl, —O—C$_{2-6}$ alkenyl, —O—C$_{2-6}$ alkynyl, NR$^{12}$R$^{12a}$, C$_{3-6}$carbocycle, and —O—C$_{3-6}$carbocycle; and t is selected from 0 and 1.

2. A compound of claim 1 or pharmaceutically acceptable salt forms thereof, wherein:

R$^2$ is selected from the group methyl substituted with 0–3 R$^{3f}$, C$_{1-5}$ alkyl substituted with 0–2 R$^4$, C$_{2-5}$ alkenyl substituted with 0–2 R$^4$, C$_{2-5}$ alkynyl substituted with 0–1 R$^4$, C$_{3-6}$ cycloalkyl substituted with 0–2 R$^{3d}$, and phenyl substituted with 0–2 R$^{3d}$, and 3–6 membered heterocyclic system containing 1–3 heteroatoms selected from the group O, N, and S, substituted with 0–2 R$^{3d}$, wherein the heterocyclic system is selected from 2-pyridyl, 3-pyridyl, 4-pyridyl, 2-furanyl, 3-furanyl, 2-thienyl, 3-thienyl, 2-oxazolyl, 2-thiazolyl, 4-isoxazolyl, 2-imidazolyl, pyrazolyl, triazolyl, 1,3-dioxolanyl, and 1,3-dioxanyl;

R$^3$ and R$^{3a}$, at each occurrence, are independently selected from the group H, C$_{1-4}$ alkyl, OH, C$_{1-4}$ alkoxy, F, Cl, Br, I, NR$^5$R$^{5a}$, NO$_2$, —CN, C(O)R$^6$, NHC(O)R$^7$, NHC(O)NR$^5$R$^{5a}$, and a 5–6 membered heteroaromatic ring containing 1–4 heteroatoms selected from the group O, N, and S;

alternatively, R$^3$ and R$^{3a}$ together form —OCH$_2$O—;

R$^{3b}$ and R$^{3c}$, at each occurrence, are independently selected from the group H, C$_{1-4}$ alkyl, OH, C$_{1-4}$ alkoxy, F, Cl, Br, I, NR$^5$R$^{5a}$, NO$_2$, —CN, C(O)R$^6$, NHC(O)R$^7$, and NHC(O)NR$^5$R$^{5a}$;

alternatively, R$^{3a}$ and R$^{3b}$ together form —OCH$_2$O—;

R$^4$ is selected from the group H, Cl, F, C$_{1-4}$ alkyl substituted with 0–2 R$^{3e}$, C$_{3-6}$ carbocycle substituted with 0–2 R$^{3e}$, phenyl substituted with 0–5 R$^{3e}$, and a 5–6 membered heterocyclic system containing 1–3 heteroatoms selected from the group O, N, and S, substituted with 0–2 R$^{3e}$;

R$^5$ and R$^{5a}$ are independently selected from the group H, CH$_3$ and C$_2$H$_5$;

R$^6$ is selected from the group H, OH, CH$_3$, C$_2$H$_5$, OCH$_3$, OC$_2$H$_5$, and NR$^5$R$^{5a}$; and R$^7$ is selected from the group CH$_3$, C$_2$H$_5$, CH(CH$_3$)$_2$, OCH$_3$, OC$_2$H$_5$, and OCH(CH$_3$)$_2$.

3. A compound of claim 2, wherein:
P is O;
Ring A is:

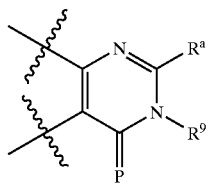 or 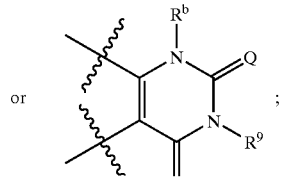

$R^a$, at each occurrence, is selected from H, $C_{1-4}$ alkyl, $C_{1-4}$ alkyl-NH—, $NH_2$;
$R^c$ is selected from H and methyl;
W is $CR^3$;
X is $CR^{3a}$;
Y is $CR^{3b}$;
Z is $CR^{3c}$;
$R^2$ is selected from the group methyl substituted with 0–3 $R^{3f}$, $C_{1-3}$ alkyl substituted with 0–2 $R^4$, $C_{2-3}$ alkenyl substituted with 0–2 $R^4$, $C_{2-3}$ alkynyl substituted with 0–1 $R^4$, and $C_{3-6}$ cycloalkyl substituted with 0–2 $R^{3d}$;
$R^3$, $R^{3a}$, $R^{3b}$, and $R^{3c}$, at each occurrence, are independently selected from the group H, $C_{1-3}$ alkyl, OH, $C_{1-3}$ alkoxy, F, Cl, Br, I, $NR^5R^{5a}$, $NO_2$, —CN, $C(O)R^6$, $NHC(O)R^7$, and $NHC(O)NR^5R^{5a}$;
alternatively, $R^3$ and $R^{3a}$ together form —OCH$_2$O—;
$R^{3e}$, at each occurrence, is independently selected from the group H, $C_{1-4}$ alkyl, —OH, $C_{1-4}$ alkoxy, $OCF_3$, F, Cl, —NR$^5$R$^{5a}$, —C(O)R$^6$, and —SO$_2$NR$^5$R$^{5a}$;
$R^{3f}$, at each occurrence, is independently selected from the group H, F, Cl, Br, I, $C_{1-4}$ alkyl, CN, —OH, —O—R$^{11}$, —O(CO)—R$^{13}$, —SR$^{11}$, —S(O)R$^{11}$, —S(O)$_2$R$^{11}$, and —NR$^{12}$R$^{12a}$;
$R^4$ is selected from the group H, Cl, F, $C_{1-4}$ alkyl substituted with 0–1 $R^{3e}$, $C_{3-5}$ carbocycle substituted with 0–2 $R^{3e}$, phenyl substituted with 0–2 $R^{3e}$, and a 5–6 membered heterocyclic system containing 1–3 heteroatoms selected from the group O, N, and S, substituted with 0–1 $R^{3e}$, wherein the heterocyclic system is selected from 2-pyridyl, 3-pyridyl, 4-pyridyl, 2-furanyl, 3-furanyl, 2-thienyl, 3-thienyl, 2-oxazolyl, 2-thiazolyl, 4-isoxazolyl, 2-imidazolyl, pyrazolyl, triazolyl, 1,3-dioxolanyl, and 1,3-dioxanyl;
$R^5$ and $R^{5a}$ are independently selected from the group H, $CH_3$ and $C_2H_5$;
$R^6$ is selected from the group H, OH, $CH_3$, $C_2H_5$, $OCH_3$, $OC_2H_5$, and $NR^5R^{5a}$;
$R^7$ is selected from the group $CH_3$, $C_2H_5$, $OCH_3$, and $OC_2H_5$;
$R^8$ is H;
$R^9$ is H, methyl, ethyl, propyl, and i-propyl;
$R^{11}$ is selected from methyl, ethyl, propyl, i-propyl, butyl, i-butyl, t-butyl, and $C_{3-6}$ carbocycle substituted with 0–2 $R^{3e}$ wherein the $C_{3-6}$ carbocycle is selected from cyclopropyl, cyclobutyl, cyclopentyl, cyclohexyl and phenyl; and
$R^{12}$ and $R^{12a}$ are independently selected from H, methyl, ethyl, propyl, i-propyl, butyl, i-butyl, t-butyl, and $C_{3-6}$ carbocycle substituted with 0–2 $R^{3e}$ wherein the $C_{3-6}$ carbocycle is selected from cyclopropyl, cyclobutyl, cyclopentyl, cyclohexyl and phenyl.

4. A compound of claim 3, or a pharmaceutically acceptable salt form thereof, wherein:
$R^2$ is selected from the group methyl substituted with 0–3 $R^{3f}$, $C_{1-3}$ alkyl substituted with 1 $R^4$, $C_{2-3}$ alkenyl substituted with 1 $R^4$, and $C_{2-3}$ alkynyl substituted with 1 $R^4$;
$R^3$, $R^{3a}$, $R^{3b}$, and $R^{3c}$, at each occurrence, are independently selected from the group H, $C_{1-3}$ alkyl, OH, $C_{1-3}$ alkoxy, F, Cl, $NR^5R^{5a}$, $NO_2$, —CN, $C(O)R^6$, $NHC(O)R^7$, and $NHC(O)NR^5R^{5a}$;
alternatively, $R^3$ and $R^{3a}$ together form —OCH$_2$O—;
$R^{3e}$, at each occurrence, is independently selected from the group $CH_3$, —OH, $OCH_3$, $OCF_3$, F, Cl, and —NR$^5$R$^{5a}$;
$R^{3f}$, at each occurrence, is independently selected from the group H, F, Cl, Br, I, $C_{1-4}$ alkyl, —OH, CN, —O—R$^{11}$, —O(CO)—R$^{13}$, and —NR$^{12}$R$^{12a}$, —SR$^{11}$, —S(O)R$^{11}$, —S(O)$_2$R$^{11}$, and —OS(O)$_2$methyl;
$R^4$ is selected from the group H, Cl, F, $CH_3$, $CH_2CH_3$, cyclopropyl substituted with 0–1 $R^{3e}$, 1-methylcyclopropyl substituted with 0–1 $R^{3e}$, cyclobutyl substituted with 0–1 $R^{3e}$, phenyl substituted with 0–2 $R^{3e}$, and a 5–6 membered heterocyclic system containing 1–3 heteroatoms selected from the group O, N, and S, substituted with 0–1 $R^{3e}$, wherein the heterocyclic system is selected from the group 2-pyridyl, 3-pyridyl, 4-pyridyl, 2-imidazolyl, pyrazolyl, triazolyl, 1,3-dioxolanyl, and 1,3-dioxanyl;
$R^5$ and $R^{5a}$ are independently selected from the group H, $CH_3$ and $C_2H_5$;
$R^6$ is selected from the group H, OH, $CH_3$, $C_2H_5$, $OCH_3$, $OC_2H_5$, and $NR^5R^{5a}$;
$R^7$ is selected from the group $CH_3$, $C_2H_5$, $OCH_3$, and $OC_2H_5$; and
$R^9$ is selected from H and methyl.

5. A compound of claim 4, or a pharmaceutically acceptable salt form thereof, wherein:
$R^2$ is selected from the group methyl substituted with 0–2 $R^{3f}$, methyl substituted with 0–2 $R^4$, ethyl substituted with 0–2 $R^4$, propyl substituted with 0–2 $R^4$, ethenyl substituted with 0–2 $R^4$, 1-propenyl substituted with 0–2 $R^4$, 2-propenyl substituted with 0–2 $R^4$, ethynyl substituted with 0–2 $R^4$, 1-propynyl substituted with 0–2 $R^4$, 2-propynyl substituted with 0–2 $R^4$, and cyclopropyl substituted with 0–1 $R^{3d}$;
$R^{3e}$, at each occurrence, is independently selected from the group $CH_3$, —OH, $OCH_3$, $OCF_3$, F, Cl, and —NR$^5$R$^{5a}$;
$R^4$ is selected from the group H, Cl, F, $CH_3$, $CH_2CH_3$, cyclopropyl substituted with 0–1 $R^{3e}$, 1-methylcyclopropyl substituted with 0–1 $R^{3e}$, cyclobutyl substituted with 0–1 $R^{3e}$, phenyl substituted with 0–2 $R^{3e}$, and a 5–6 membered heterocyclic system containing 1–3 heteroatoms selected from the group O, N, and S, substituted with 0–1 $R^{3e}$, wherein the heterocyclic system is selected from the group 2-pyridyl, 3-pyridyl, 4-pyridyl, 2-imidazolyl, pyrazolyl, triazolyl, 1,3-dioxolanyl, and 1,3-dioxanyl;
$R^5$ and $R^{5a}$ are independently selected from the group H, $CH_3$ and $C_2H_5$;
$R^6$ is selected from the group H, OH, $CH_3$, $C_2H_5$, $OCH_3$, $OC_2H_5$, and $NR^5R^{5a}$;
$R^7$ is selected from the group $CH_3$, $C_2H_5$, $OCH_3$, and $OC_2H_5$;

$R^8$ is H.

6. A compound of claim 5, or a pharmaceutically acceptable salt form thereof, wherein:

$R^1$ is selected from methyl, ethyl, propyl, i-propyl, butyl, cyclopropyl, $CF_3$, $CF_2CH_3$, CN, and hydroxymethyl;

$R^2$ is selected from the group methyl substituted with 0–2 $R^{3f}$, methyl substituted with 0–2 $R^4$, ethyl substituted with 0–2 $R^4$, propyl substituted with 0–1 $R^4$, ethenyl substituted with 0–2 $R^4$, 1-propenyl substituted with 0–2 $R^4$, 2-propenyl substituted with 0–2 $R^4$, ethynyl substituted with 0–2 $R^4$, 1-propynyl substituted with 0–2 $R^4$;

$R^3$, $R^{3b}$, and $R^{3c}$ are H;

$R^{3e}$ is $CH_3$;

$R^{3f}$, at each occurrence, is independently selected from the group H, F, Cl, Br, I, $C_{1-4}$ alkyl, CN, —OH, —O—$R^{11}$, —$SR^{11}$, —S(O)$R^{11}$, —S(O)$_2R^{11}$, and —$NR^{12}R^{12a}$;

$R^4$ is selected from the group H, cyclopropyl substituted with 0–1 $R^{3e}$, and a 5–6 membered heterocyclic system containing 1–3 heteroatoms selected from the group O, N, and S, substituted with 0–1 $R^{3e}$, wherein the heterocyclic system is selected from the group 2-pyridyl, 3-pyridyl, 4-pyridyl, 2-imidazolyl, pyrazolyl, triazolyl, 1,3-dioxolanyl, and 1,3-dioxanyl;

$R^{12}$ and $R^{12a}$ are independently selected from H, methyl, ethyl, propyl, and i-propyl, and $C_{3-6}$ carbocycle substituted with 0–2 $R^{3e}$ wherein the $C_{3-6}$ carbocycle is selected from cyclopropyl.

7. A compound of claim 5, or a pharmaceutically acceptable salt form thereof, wherein:

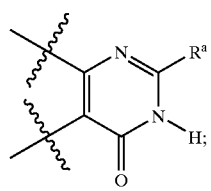

ring A is $R^a$ is H, methyl, ethyl, propyl, and i-propyl;

$R^1$ is $CF_3$;

$R^2$ is selected from methyl substituted with 0–1 $R^{3f}$, ethyl, propyl, i-propyl, and butyl;

W is CH;

X is $CR^{3a}$;

Y is CH;

Z is CH;

$R^{3a}$ is selected from H, F, Cl, Br, and CN;

$R^{3f}$ is —O—$R^{11}$;

$R^8$ is H; and $R^{11}$ is selected from methyl, ethyl, propyl, i-propyl, butyl, s-butyl, i-butyl, and t-butyl.

8. A compound of claim 1, or a pharmaceutically acceptable salt form thereof, wherein the compound is of formula (Ic):

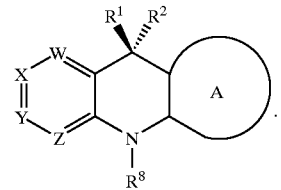

9. A compound of claim 1, or a pharmaceutically acceptable salt form thereof, wherein the compound of formula (I) is selected from:

10-Butyl-8-chloro-10-(trifluoromethyl)-5,10-dihydropyrimido[5,4-b]quinolin-4(3H)-one;

10-Butyl-8-cyano-10-(trifluoromethyl)-5,10-dihydropyrimido[5,4-b]quinolin-4(3H)-one;

8-Chloro-10-(isopropoxymethyl)-10-(trifluoromethyl)-5,10-dihydropyrimido[5,4-b]quinolin-4(3H)-one;

8-Cyano-10-(isopropoxymethyl)-10-(trifluoromethyl)-5,10-dihydropyrimido[5,4-b]quinolin-4(3H)-one;

10-Butyl-8-chloro-2-methyl-10-(trifluoromethyl)-5,10-dihydropyrimido[5,4-b]quinolin-4(3H)-one;

8-Chloro-10-(isopropoxymethyl)-2-methyl-10-(trifluoromethyl)-5,10-dihydropyrimido[5,4-b]quinolin-4(3H)-one;

8-Cyano-10-(isopropoxymethyl)-2-methyl-10-(trifluoromethyl)-5,10-dihydropyrimido[5,4-b]quinolin-4(3H)-one;

8-Chloro-10-(2-cyclopropylethyl)-10-(trifluoromethyl)-5,10-dihydropyrimido[5,4-b]quinolin-4(3H)-one;

8-Cyano-10-(2-cyclopropylethyl)-10-(trifluoromethyl)-5,10-dihydropyrimido[5,4-b]quinolin-4(3H)-one; and 10-(4-Bromobenzyl)-8-chloro-10-(trifluoromethyl)-5,10-dihydropyrimido[5,4-b]quinolin-4(3H)-one.

10. A compound of claim 1, or a pharmaceutically acceptable from thereof, wherein the compound of formula (I) is B-Chloro-10-(isopropoxmethyl)-10-(trifluoromethyl)-5,10-dihydropyrimido [5,4-b] quinolin-4 (3H)-one.

11. A compound of claim 1, or a pharmaceutically acceptable salt form thereof, wherein the compound of formula (I) is 8-Cyano-10-(isopropoxymethyl)-10-(trifluoromethyl)-5,10-dihydropyrimido[5,4-b] quinolin-4(3H)-one.

12. A compound of claim 1, or a pharmaceutically acceptable salt form thereof, wherein the compound of formula (I) is 8-Cyano-10-(isopropoxymethyl)-2-methyl-10-(trifluoromethyl)-5,10-dihydropyrimido[5,4-b] quinolin-4 (3H)-one.

13. A compound of claim 1, or a pharmaceutically acceptable salt form thereof, wherein the compound of formula (I) is 8-Cyano-10-(2-cyclopropylethyl)-10-(trifluoromethyl)-5,10-dihydropyrimido-[5,4-b]quinolin-4(3H)-one.

14. A compound of claim 1, or a pharmaceutically acceptable salt form thereof, wherein the compound of formula (I) is (R)-8-Cyano-10-(isopropoxymethyl)-10-(trifluoromethyl)-5,10-dihydropyrimido-[5,4-b]quinolin-4 (3H)-one.

15. A pharmaceutical composition comprising a pharmaceutically acceptable carrier and a therapeutically effective amount of a compound according claim 1or pharmaceutically acceptable salt form thereof.

16. A pharmaceutical composition comprising a pharmaceutically acceptable carrier and a therapeutically effective amount of a compound according to claim 10 or pharmaceutically acceptable salt form thereof.

17. A pharmaceutical composition comprising a pharmaceutically acceptable carrier and a therapeutically effective amount of a compound according to claim 11 or pharmaceutically acceptable salt form thereof.

18. A pharmaceutical composition comprising a pharmaceutically acceptable carrier and a therapeutically effective amount of a compound according to claim 12 or pharmaceutically acceptable salt form thereof.

19. A pharmaceutical composition comprising a pharmaceutically acceptable carrier and a therapeutically effective amount of a compound according to claim 13 or pharmaceutically acceptable salt form thereof.

20. A pharmaceutical composition comprising a pharmaceutically acceptable carrier and a therapeutically effective amount of a compound according to claim 14 or pharmaceutically acceptable salt form thereof.

21. A method for treating HIV infection which comprises administering to a host in need of such treatment a therapeutically effective amount of a compound according to claims 1 or pharmaceutically acceptable salt form thereof.

22. A method of treating HIV infection which comprises administering, in combination, to a host in need thereof a therapeutically effective amount of:
   (a) a compond according to claims 1; and,
   (b) at least one compound selected from the group consisting of HIV reverse transcriptase inhibitors, HIV protease inhibitors, fusion inhibitors, and CCR-5 inhibitors.

23. A method of claim 22, wherein the reverse transcriptase inhibitor is selected from the group AZT, ddC, ddI, d4T, 3TC, delavirdine, efavirenz, nevirapine, trovirdine, MKC-442, HBY 097, HBY1293, GW867, ACT, UC-781, UC-782, RD4-2025, MEN 10979, AG1549 (S1153), TMC-120, TMC-125, Calanolide A, and PMPA, and the protease inhibitor is selected from the group saquinavar, ritonavir, indinavir, amprenavir, nelfinavir, palinavir, BMS232623, GS3333, KNI-413, KNI-272, LG-71350, CGP- 61755, PD 173606, PD 177298, PD 178390, PD 178392, U-120690, ABT-378, DMP-450, AG-1776, VX-175, MK-944, and VX-478, the CCR-5, inhibitor is selected from TAK-779 (Takeda), SC-351125 (SCH-C, Schering) and SCH-D (Schering), and the fusion inhibitor is selected from T-20 and T1249.

24. A method of claim 23, wherein the reverse transcriptase inhibitor is selected from the group AZT, efavirenz, and 3TC and the protease inhibitor is selected from the group saquinavir, ritonavir, nelfinavir, and indinavir.

25. A method of claim 24, wherein the reverse transcriptase inhibitor is AZT.

26. A method of claim 25, wherein the protease inhibitor is indinavir.

27. A method for treating HIV infection which comprises administering to a host in need of such treatment a therapeutically effective amount of a compound according to claims 10 or pharmaceutically acceptable salt form thereof.

28. A method for treating HIV infection which comprises administering to a host in need of such treatment a therapeutically effective amount of a compound according to claims 11 or pharmaceutically acceptable salt form thereof.

29. A method for treating HIV infection which comprises administering to a host in need of such treatment a therapeutically effective amount of a compound according to claims 12 or pharmaceutically acceptable salt form thereof.

30. A method for treating HIV infection which comprises administering to a host in need of such treatment a therapeutically effective amount of a compound according to claims 13 or pharmaceutically acceptable salt form thereof.

31. A method for treating HIV infection which comprises administering to a host in need of such treatment a therapeutically effective amount of a compound according to claims 14 or pharmaceutically acceptable salt form thereof.

32. A pharmaceutical kit useful for the treatment of HIV infection, which comprises a therapeutically effective amount of:
   (a) a compound according to claims 1; and,
   (b) at least one compound selected from the group consisting of HIV reverse transcriptase inhibitors and HIV protease inhibitors, in one or more sterile containers.

* * * * *

UNITED STATES PATENT AND TRADEMARK OFFICE
CERTIFICATE OF CORRECTION

PATENT NO. : 6,844,340 B2
DATED : January 18, 2005
INVENTOR(S) : Christine M. Tarby It is certified that error appears in the above-identified patent and that said Letters Patent is hereby corrected as shown below:

<u>Column 43,</u>
Line 16, replace "$R^{3d}$" with -- $R^{3b}$ --

<u>Column 48,</u>
Line 40, replace "B-Chloro-" with -- 8-Chloro --

<u>Column 49,</u>
Line 38, replace "U-120690" with -- U-140690 --

Signed and Sealed this

Seventeenth Day of May, 2005

JON W. DUDAS
*Director of the United States Patent and Trademark Office*